US012569247B2

(12) United States Patent
Leimbach et al.

(10) Patent No.: US 12,569,247 B2
(45) Date of Patent: Mar. 10, 2026

(54) SYSTEMS AND METHODS FOR CONTROLLING A SEGMENTED CIRCUIT

(71) Applicant: Cilag GmbH International, Zug (CH)

(72) Inventors: Richard L. Leimbach, Cincinnati, OH (US); Shane R. Adams, Lebanon, OH (US); Mark D. Overmyer, Cincinnati, OH (US); Brett E. Swensgard, West Chester, OH (US); Thomas W. Lytle, IV, Liberty Township, OH (US); Frederick E. Shelton, IV, Hillsboro, OH (US); Kevin L. Houser, Springboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 19/024,230

(22) Filed: Jan. 16, 2025

(65) Prior Publication Data

US 2025/0228558 A1 Jul. 17, 2025

Related U.S. Application Data

(63) Continuation of application No. 17/984,594, filed on Nov. 10, 2022, now Pat. No. 12,232,723, which is a (Continued)

(51) Int. Cl.

*A61B 17/00* (2006.01)
*A61B 17/068* (2006.01)

(Continued)

(52) U.S. Cl.

CPC ...... *A61B 17/068* (2013.01); *A61B 17/07207* (2013.01); *B25F 3/00* (2013.01); *B25F 5/00* (2013.01); *G05F 1/563* (2013.01); *G05F 1/61* (2013.01); *G05F 5/00* (2013.01); *G06F 1/3296* (2013.01); *H02H 3/087* (2013.01); *H02H 3/18* (2013.01); *H02H 7/1213* (2013.01); *H02H 11/006* (2013.01); *A61B 2017/00017* (2013.01);

(Continued)

(58) Field of Classification Search

CPC ................ A61B 17/068; A61B 17/072; A61B 2017/00017; A61B 2017/00137

See application file for complete search history.

(56) References Cited

U.S. PATENT DOCUMENTS 4,691,703 A 9/1987 Auth et al.
5,001,649 A 3/1991 Lo et al.

(Continued)

FOREIGN PATENT DOCUMENTS

EP 1558161 A1 8/2005
JP 2001-69758 A 3/2001
JP 2007-97252 A 4/2007

*Primary Examiner* — Gloria R Weeks

(74) *Attorney, Agent, or Firm* — Lempia Summerfield Katz LLC

(57) ABSTRACT

The present disclosure provides a method for controlling a surgical instrument. The method includes connecting a power assembly to a control circuit, wherein the power assembly is configured to provide a source voltage, energizing, by the power assembly, a voltage boost convertor circuit configured to provide a set voltage greater than the source voltage, and energizing, by the voltage boost convertor, one or more voltage convertors configured to provide one or more operating voltages to one or more circuit components.

20 Claims, 20 Drawing Sheets

Related U.S. Application Data continuation of application No. 16/017,403, filed on Jun. 25, 2018, now Pat. No. 11,497,488, which is a continuation of application No. 15/727,332, filed on Oct. 6, 2017, now Pat. No. 10,117,653, which is a continuation of application No. 14/226,081, filed on Mar. 26, 2014, now Pat. No. 9,804,618.

(51) Int. Cl.

| | |
|---|---|
| ***A61B 17/072*** | (2006.01) |
| ***B25F 3/00*** | (2006.01) |
| ***B25F 5/00*** | (2006.01) |
| ***G05F 1/563*** | (2006.01) |
| ***G05F 1/61*** | (2006.01) |
| ***G05F 5/00*** | (2006.01) |
| ***G06F 1/3296*** | (2019.01) |
| ***H02H 3/087*** | (2006.01) |
| ***H02H 3/18*** | (2006.01) |
| ***H02H 7/12*** | (2006.01) |
| ***H02H 11/00*** | (2006.01) |
| *A61B 17/29* | (2006.01) |
| *A61B 90/00* | (2016.01) |
| *H02M 1/00* | (2006.01) |

(52) U.S. Cl.

CPC ............... *A61B 2017/00022* (2013.01); *A61B 2017/00075* (2013.01); *A61B 2017/00084* (2013.01); *A61B 2017/00115* (2013.01); *A61B 2017/00123* (2013.01); *A61B 2017/00132* (2013.01); *A61B 2017/00199* (2013.01); *A61B 2017/00221* (2013.01); *A61B 2017/00353* (2013.01); *A61B 2017/00398* (2013.01); *A61B 2017/0046* (2013.01); *A61B 2017/00734* (2013.01); *A61B 2017/07285* (2013.01); *A61B 2017/2927* (2013.01); *A61B 2090/0803* (2016.02); *A61B 2090/0808* (2016.02); *A61B 2090/081* (2016.02); *A61B 2090/0811* (2016.02); *A61B 2090/0813* (2016.02); *H02M 1/0067* (2021.05)

(56) References Cited

U.S. PATENT DOCUMENTS

| | | | | |
|---|---|---|---|---|
| 6,471,659 | B2 | 10/2002 | Eggers et al. | |
| 6,998,816 | B2 | 2/2006 | Wieck et al. | |
| 7,202,653 | B2 | 4/2007 | Pai | |
| 7,249,267 | B2 | 7/2007 | Chapuis | |
| 7,793,812 | B2 | 9/2010 | Moore et al. | |
| 8,063,619 | B2 | 11/2011 | Zhu et al. | |
| 8,085,013 | B2 | 12/2011 | Wei et al. | |
| 8,179,705 | B2 | 5/2012 | Chapuis | |
| 8,210,411 | B2 * | 7/2012 | Yates | A61B 17/3205 227/19 |
| 8,228,048 | B2 | 7/2012 | Spencer | |
| 8,444,036 | B2 * | 5/2013 | Shelton, IV | A61B 17/068 227/176.1 |
| 8,523,043 | B2 * | 9/2013 | Ullrich | A61B 17/072 227/19 |
| 8,627,994 | B2 | 1/2014 | Zemlok et al. | |
| 8,808,311 | B2 | 8/2014 | Heinrich et al. | |
| 8,960,520 | B2 | 2/2015 | McCuen | |
| 8,967,443 | B2 | 3/2015 | McCuen | |
| 9,119,657 | B2 | 9/2015 | Shelton, IV et al. | |
| 9,123,286 | B2 | 9/2015 | Park | |
| 9,232,979 | B2 | 1/2016 | Parihar et al. | |
| 9,265,585 | B2 | 2/2016 | Wingardner et al. | |
| 9,314,291 | B2 | 4/2016 | Schall et al. | |
| 9,332,987 | B2 | 5/2016 | Leimbach et al. | |
| 9,507,399 | B2 | 11/2016 | Chien | |
| 9,526,921 | B2 | 12/2016 | Kimball et al. | |
| 9,629,629 | B2 | 4/2017 | Leimbach et al. | |
| 9,649,110 | B2 | 5/2017 | Parihar et al. | |
| 9,690,362 | B2 | 6/2017 | Leimbach et al. | |
| 9,844,368 | B2 | 12/2017 | Boudreaux et al. | |
| 9,888,919 | B2 | 2/2018 | Leimbach et al. | |
| 10,524,785 | B2 | 1/2020 | Zemlok et al. | |
| 2006/0176031 | A1 | 8/2006 | Forman et al. | |
| 2009/0090763 | A1 | 4/2009 | Zemlok et al. | |
| 2011/0022032 | A1 | 1/2011 | Zemlok et al. | |
| 2013/0103024 | A1 * | 4/2013 | Monson | H02J 7/00 606/33 |
| 2013/0126581 | A1 * | 5/2013 | Yates | A61B 17/1155 227/175.1 |
| 2013/0193188 | A1 * | 8/2013 | Shelton, IV | A61B 17/07207 227/175.2 |
| 2013/0211397 | A1 * | 8/2013 | Parihar | A61B 90/10 606/130 |
| 2013/0214025 | A1 * | 8/2013 | Zemlok | A61B 17/07207 227/175.1 |
| 2015/0277471 | A1 * | 10/2015 | Leimbach | G05F 1/61 323/299 |
| 2023/0309992 | A1 | 10/2023 | Leimbach et al. | |

* cited by examiner

SYSTEMS AND METHODS FOR CONTROLLING A SEGMENTED CIRCUIT

CROSS-REFERENCE TO RELATED APPLICATIONS

This application is a continuation application claiming priority under 35 U.S.C. § 120 to U.S. patent application Ser. No. 17/984,594, entitled SYSTEMS AND METHODS FOR CONTROLLING A SEGMENTED CIRCUIT, filed Nov. 10, 2022, now U.S. Patent Application Publication No. 2023/0309992, which is a continuation application claiming priority under 35 U.S.C. § 120 to U.S. patent application Ser. No. 16/017,403, entitled SYSTEMS AND METHODS FOR CONTROLLING A SEGMENTED CIRCUIT, filed Jun. 25, 2018, which issued on Nov. 15, 2022 as U.S. Pat. No. 11,497,488, which is a continuation application claiming priority under 35 U.S.C. § 120 to U.S. patent application Ser. No. 15/727,332, entitled SYSTEMS AND METHODS FOR CONTROLLING A SEGMENTED CIRCUIT, filed Oct. 6, 2017, which issued on Nov. 6, 2018 as U.S. Pat. No. 10,117,653, which is a continuation application claiming priority under 35 U.S.C. § 120 to U.S. patent application Ser. No. 14/226,081, entitled SYSTEMS AND METHODS FOR CONTROLLING A SEGMENTED CIRCUIT, filed Mar. 26, 2014, which issued on Oct. 31, 2017 as U.S. Pat. No. 9,804,618, the entire disclosures of which are hereby incorporated by reference herein.

BACKGROUND

The present invention relates to surgical instruments and, in various circumstances, to surgical stapling and cutting instruments and staple cartridges therefor that are designed to staple and cut tissue.

BRIEF DESCRIPTION OF THE DRAWINGS

The features and advantages of this invention, and the manner of attaining them, will become more apparent and the invention itself will be better understood by reference to the following description of instances of the invention taken in conjunction with the accompanying drawings, wherein.

DETAILED DESCRIPTION

Figure 1:
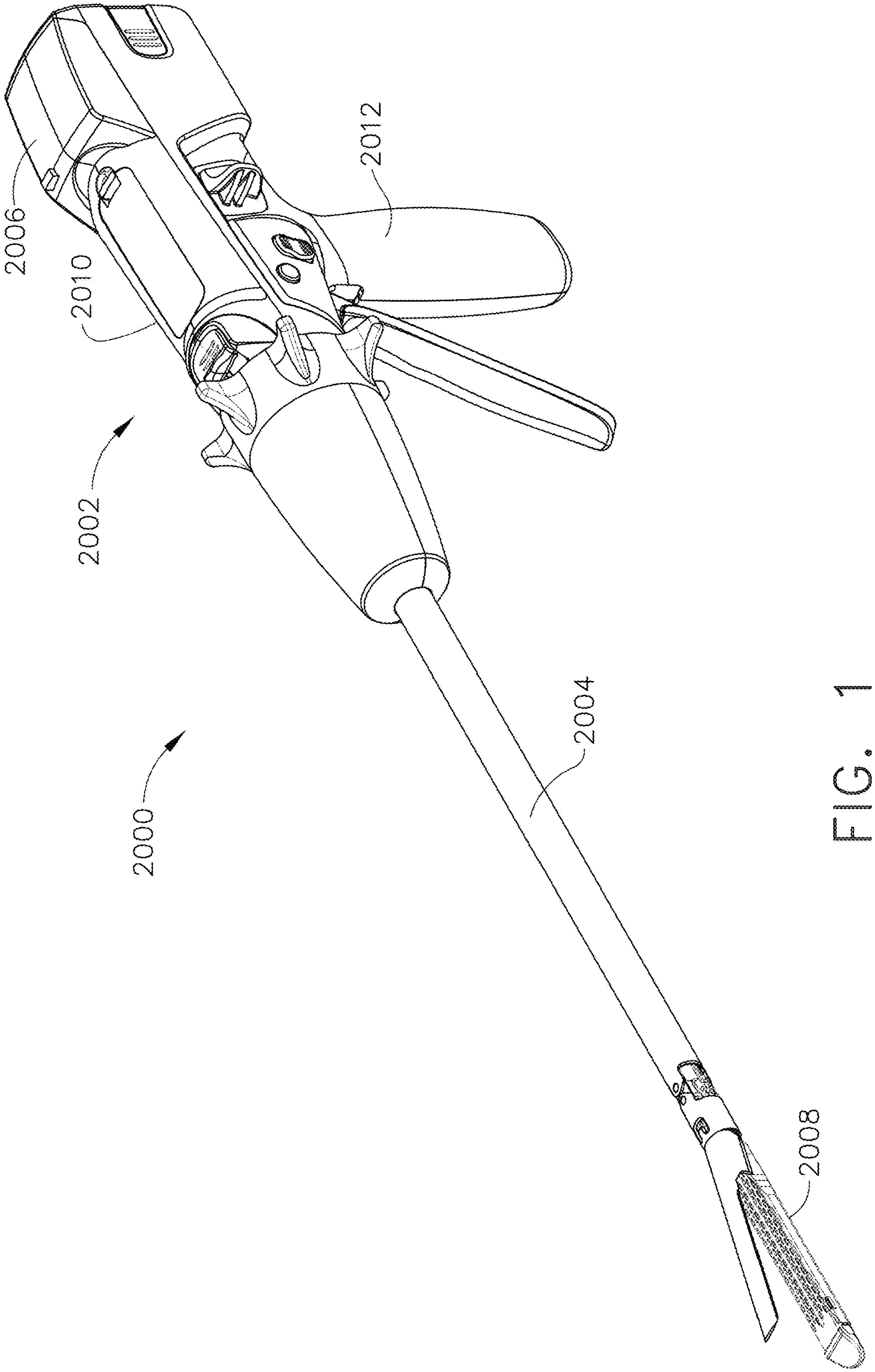
FIG. 1 is a perspective view of a surgical instrument comprising a power assembly, a handle assembly, and an interchangeable shaft assembly.

Applicant of the present application owns the following patent applications that were filed on Mar. 1, 2013 and which are each herein incorporated by reference in their respective entireties:

- U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;
- U.S. patent application Ser. No. 13/782,323, entitled ROTARY POWERED ARTICULATION JOINTS FOR SURGICAL INSTRUMENTS, now U.S. Patent Application Publication No. 2014/0246472;
- U.S. patent application Ser. No. 13/782,338, entitled THUMBWHEEL SWITCH ARRANGEMENTS FOR SURGICAL INSTRUMENTS, now U.S. Patent Application Publication No. 2014/0249557;
- U.S. patent application Ser. No. 13/782,499, entitled ELECTROMECHANICAL SURGICAL DEVICE WITH SIGNAL RELAY ARRANGEMENT, now U.S. Pat. No. 9,358,003;
- U.S. patent application Ser. No. 13/782,460, entitled MULTIPLE PROCESSOR MOTOR CONTROL FOR MODULAR SURGICAL INSTRUMENTS, now U.S. Pat. No. 9,554,794;
- U.S. patent application Ser. No. 13/782,358, entitled JOYSTICK SWITCH ASSEMBLIES FOR SURGICAL INSTRUMENTS, now U.S. Pat. No. 9,326,767;
- U.S. patent application Ser. No. 13/782,481, entitled SENSOR STRAIGHTENED END EFFECTOR DURING REMOVAL THROUGH TROCAR, now U.S. Pat. No. 9,468,438;
- U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;
- U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986 are hereby incorporated by reference in their entireties.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent applications that were filed on Mar. 26, 2014 and are each herein incorporated by reference in their respective entireties:

U.S. patent application Ser. No. 14/226,142, entitled SURGICAL INSTRUMENT COMPRISING A SENSOR SYSTEM, now U.S. Pat. No. 9,913,642;

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAIL-OUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Patent Application Publication No. 2015/0280384.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 2:
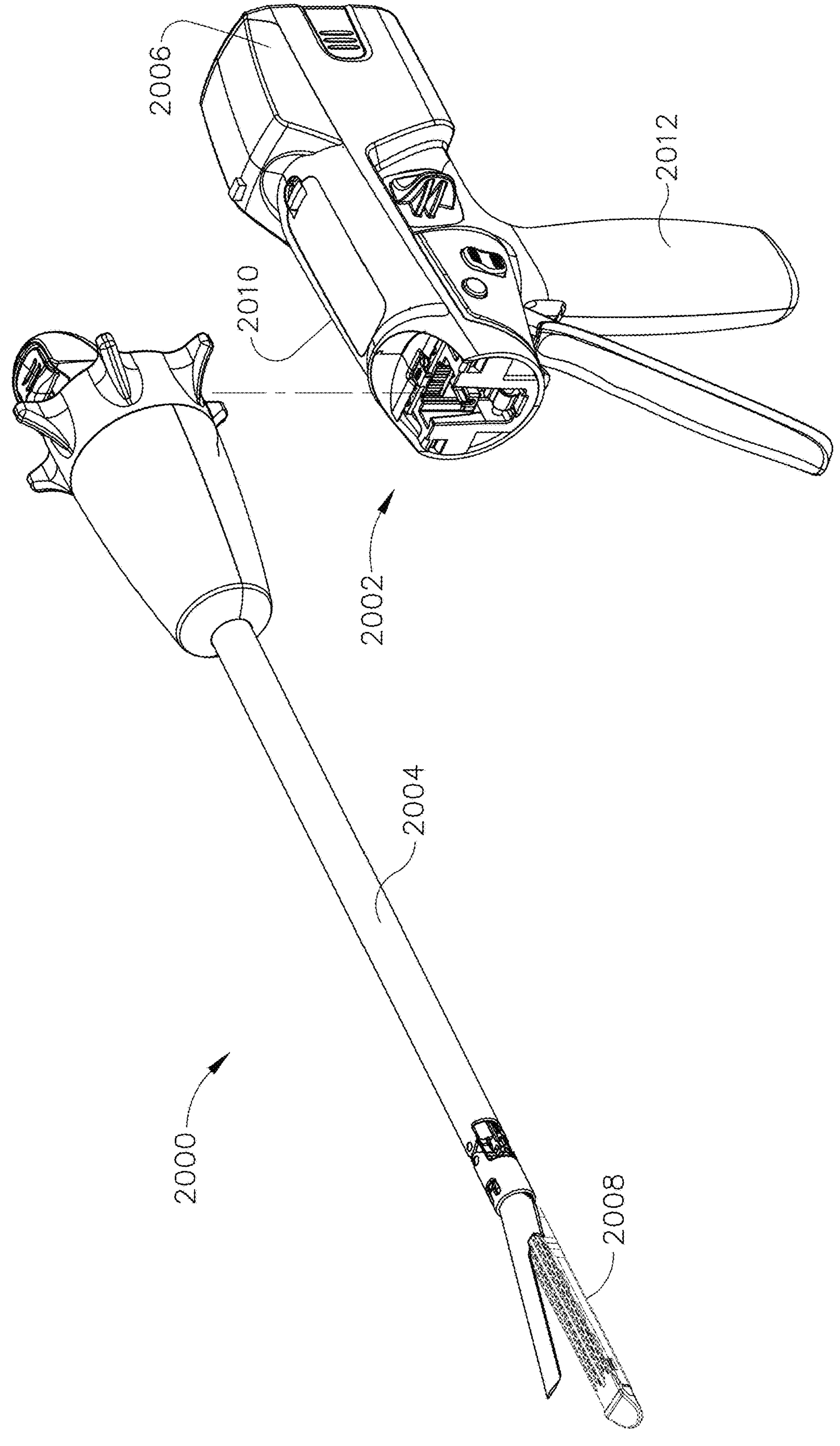
FIG. 2 is perspective view of the surgical instrument of FIG. 1 with the interchangeable shaft assembly separated from the handle assembly.

FIGS. 1-3B generally depict a motor-driven surgical fastening and cutting instrument 2000. As illustrated in FIGS. 1 and 2, the surgical instrument 2000 may include a handle assembly 2002, a shaft assembly 2004, and a power assembly 2006 ("power source," "power pack," or "battery pack"). The shaft assembly 2004 may include an end effector 2008 which, in certain circumstances, can be configured to act as an endocutter for clamping, severing, and/or stapling tissue, although, in other embodiments, different types of end effectors may be used, such as end effectors for other types of surgical devices, graspers, cutters, staplers, clip appliers, access devices, drug/gene therapy devices, ultrasound devices, RF device, and/or laser devices, for example. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008, the entire disclosures of which are incorporated herein by reference in their entirety.

Figure 3A:
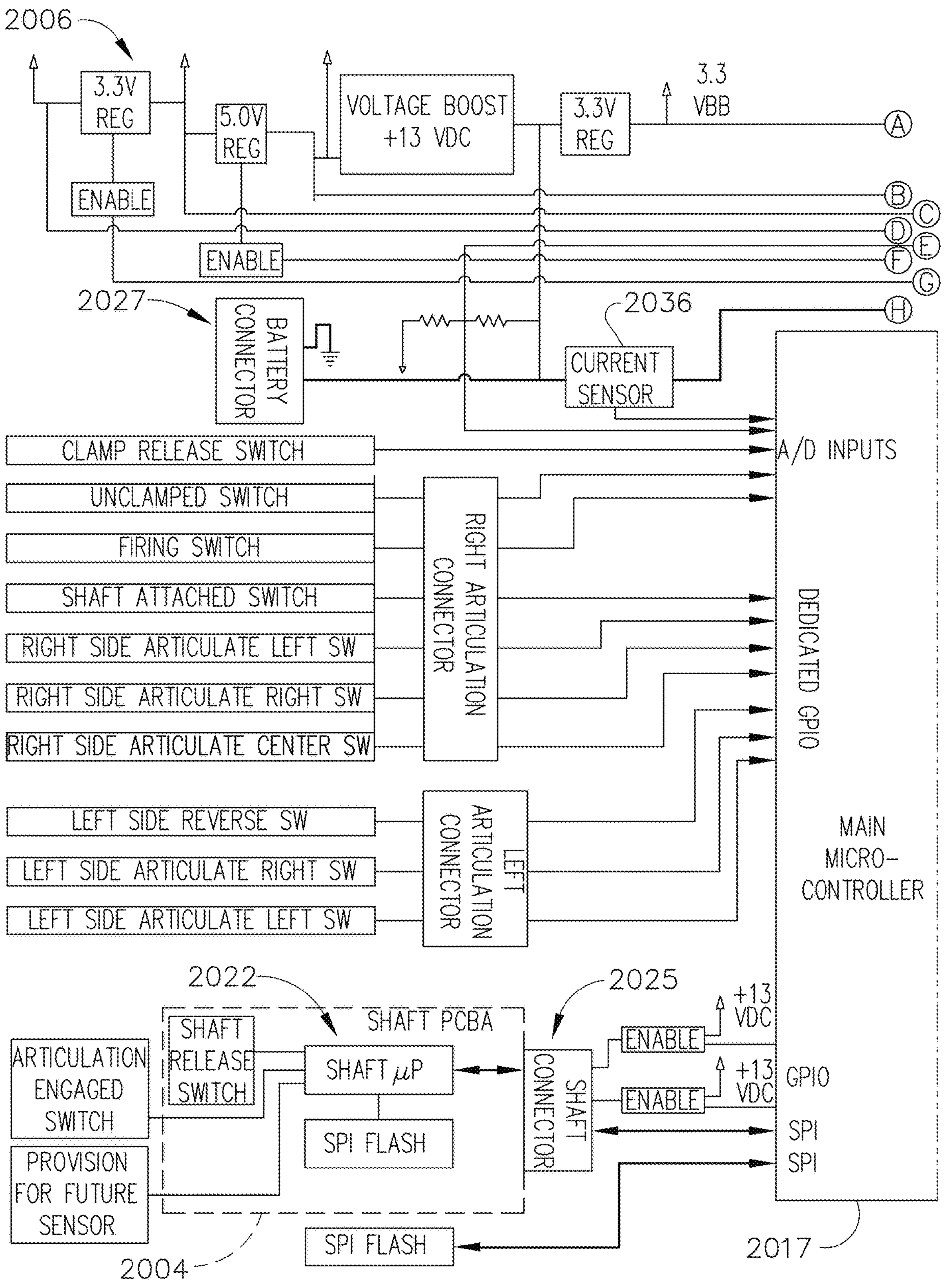
FIGS. 3A and 3B illustrate a circuit diagram of the surgical instrument of FIG. 1.
Figure 3B:
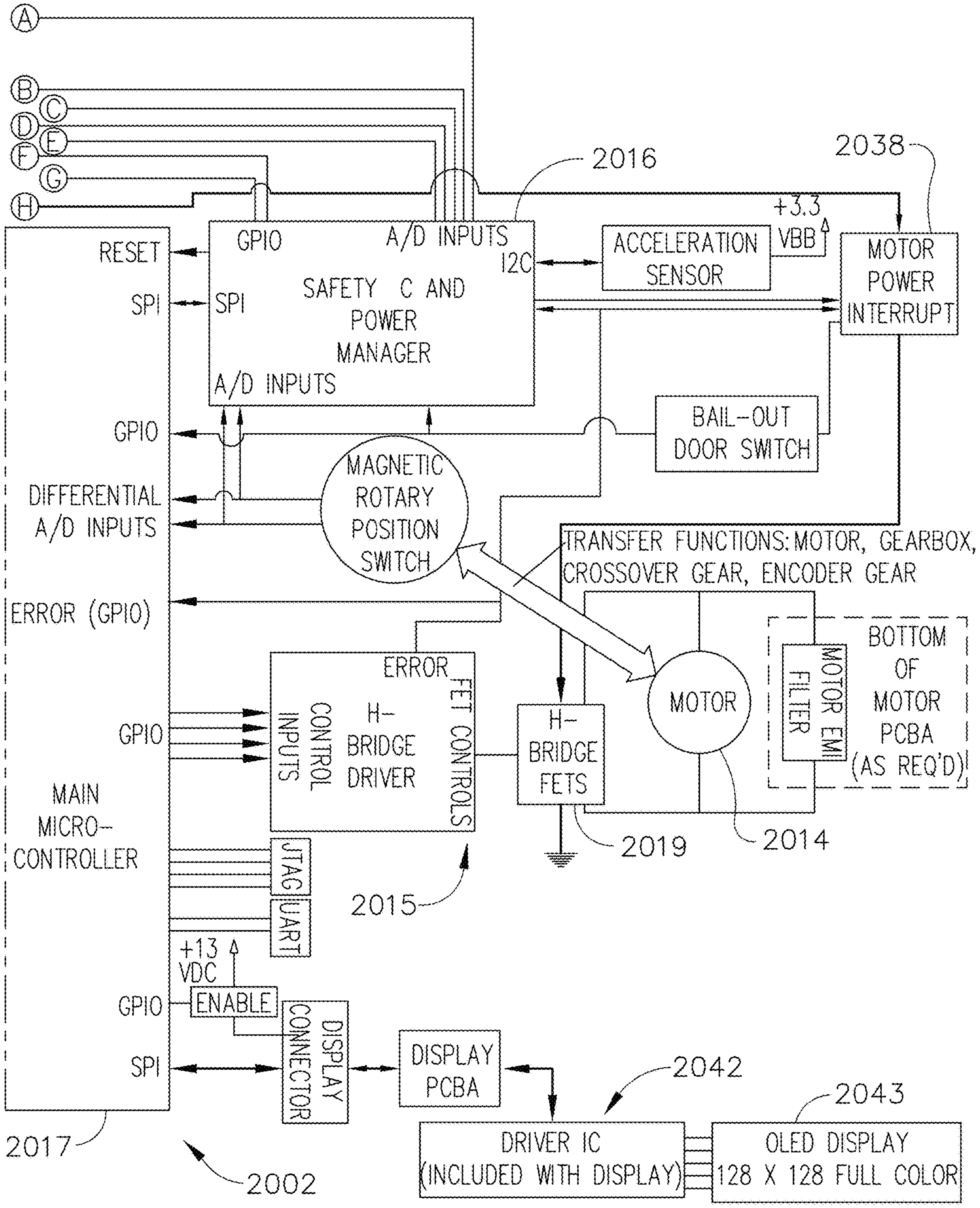

Referring primarily to FIGS. 2, 3A and 3B, the handle assembly 2002 can be employed with a plurality of interchangeable shaft assemblies such as, for example, the shaft assembly 2004. Such interchangeable shaft assemblies may comprise surgical end effectors such as, for example, the end effector 2008 that can be configured to perform one or more surgical tasks or procedures. Examples of suitable interchangeable shaft assemblies are disclosed in U.S. Provisional Patent Application Ser. No. 61/782,866, entitled CONTROL SYSTEM OF A SURGICAL INSTRUMENT, and filed Mar. 14, 2013, the entire disclosure of which is hereby incorporated by reference herein in its entirety.

Referring primarily to FIG. 2, the handle assembly 2002 may comprise a housing 2010 that consists of a handle 2012 that may be configured to be grasped, manipulated and actuated by a clinician. However, it will be understood that the various unique and novel arrangements of the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. For example, the interchangeable shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, which is incorporated by reference herein in its entirety.

Referring again to FIG. 2, the handle assembly 2002 may operably support a plurality of drive systems therein that can be configured to generate and apply various control motions to corresponding portions of the interchangeable shaft assembly that is operably attached thereto. For example, the handle assembly 2002 can operably support a first or closure drive system, which may be employed to apply closing and opening motions to the shaft assembly 2004 while operably attached or coupled to the handle assembly 2002. In at least one form, the handle assembly 2002 may operably support a firing drive system that can be configured to apply firing motions to corresponding portions of the interchangeable shaft assembly attached thereto.

Referring primarily to FIGS. 3A and 3B, the handle assembly 2002 may include a motor 2014 which can be controlled by a motor driver 2015 and can be employed by the firing system of the surgical instrument 2000. In various forms, the motor 2014 may be a DC brushed driving motor having a maximum rotation of, approximately, 25,000 RPM, for example. In other arrangements, the motor 2014 may include a brushless motor, a cordless motor, a synchronous motor, a stepper motor, or any other suitable electric motor. In certain circumstances, the motor driver 2015 may comprise an H-Bridge field-effect transistors (FETs) 2019, as illustrated in FIGS. 3A and 3B, for example. The motor 2014 can be powered by the power assembly 2006 (FIGS. 3A and 3B) which can be releasably mounted to the handle assembly 2002 for supplying control power to the surgical instrument 2000. The power assembly 2006 may comprise a battery which may include a number of battery cells connected in series that can be used as the power source to power the surgical instrument 2000. In certain circumstances, the battery cells of the power assembly 2006 may be replaceable and/or rechargeable. In at least one example, the battery cells can be Lithium-Ion batteries which can be separably couplable to the power assembly 2006.

The shaft assembly 2004 may include a shaft assembly controller 2022 which can communicate with the power management controller 2016 through an interface while the shaft assembly 2004 and the power assembly 2006 are coupled to the handle assembly 2002. For example, the interface may comprise a first interface portion 2025 which may include one or more electric connectors for coupling engagement with corresponding shaft assembly electric connectors and a second interface portion 2027 which may include one or more electric connectors for coupling engagement with corresponding power assembly electric connectors to permit electrical communication between the shaft assembly controller 2022 and the power management controller 2016 while the shaft assembly 2004 and the power assembly 2006 are coupled to the handle assembly 2002. One or more communication signals can be transmitted through the interface to communicate one or more of the power requirements of the attached interchangeable shaft assembly 2004 to the power management controller 2016. In response, the power management controller may modulate the power output of the battery of the power assembly 2006, as described below in greater detail, in accordance with the power requirements of the attached shaft assembly 2004. In certain circumstances, one or more of the electric connectors may comprise switches which can be activated after mechanical coupling engagement of the handle assembly 2002 to the shaft assembly 2004 and/or to the power assembly 2006 to allow electrical communication between the shaft assembly controller 2022 and the power management controller 2016.

In certain circumstances, the interface can facilitate transmission of the one or more communication signals between the power management controller 2016 and the shaft assembly controller 2022 by routing such communication signals through a main controller 2017 residing in the handle assembly 2002, for example. In other circumstances, the interface can facilitate a direct line of communication between the power management controller 2016 and the shaft assembly controller 2022 through the handle assembly 2002 while the shaft assembly 2004 and the power assembly 2006 are coupled to the handle assembly 2002.

In one instance, the main microcontroller 2017 may be any single core or multicore processor such as those known under the trade name ARM Cortex by Texas Instruments. In one instance, the surgical instrument 2000 may comprise a power management controller 2016 such as, for example, a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one instance, the safety processor may be configured specifically for IEC 61508 and ISO 26262 safety critical applications, among others, to provide advanced integrated safety features while delivering scalable performance, connectivity, and memory options.

In certain instances, the microcontroller 2017 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. The present disclosure should not be limited in this context.

The power assembly 2006 may include a power management circuit which may comprise the power management controller 2016, a power modulator 2038, and a current sense circuit 2036. The power management circuit can be configured to modulate power output of the battery based on the power requirements of the shaft assembly 2004 while the shaft assembly 2004 and the power assembly 2006 are coupled to the handle assembly 2002. For example, the power management controller 2016 can be programmed to control the power modulator 2038 of the power output of the power assembly 2006 and the current sense circuit 2036 can be employed to monitor power output of the power assembly 2006 to provide feedback to the power management controller 2016 about the power output of the battery so that the power management controller 2016 may adjust the power output of the power assembly 2006 to maintain a desired output.

It is noteworthy that the power management controller 2016 and/or the shaft assembly controller 2022 each may comprise one or more processors and/or memory units which may store a number of software modules. Although certain modules and/or blocks of the surgical instrument 2000 may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In certain instances, the surgical instrument 2000 may comprise an output device 2042 which may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 2042 may comprise a display 2043 which may be included in the handle assembly 2002. The shaft assembly controller 2022 and/or the power management controller 2016 can provide feedback to a user of the surgical instrument 2000 through the output device 2042. The interface 2024 can be configured to connect the shaft assembly controller 2022 and/or the power management controller 2016 to the output device 2042. The reader will appreciate that the output device 2042 can instead be integrated with the power assembly 2006. In such circumstances, communication between the output device 2042 and the shaft assembly controller 2022 may be accomplished through the interface 2024 while the shaft assembly 2004 is coupled to the handle assembly 2002.

Figure 4A:
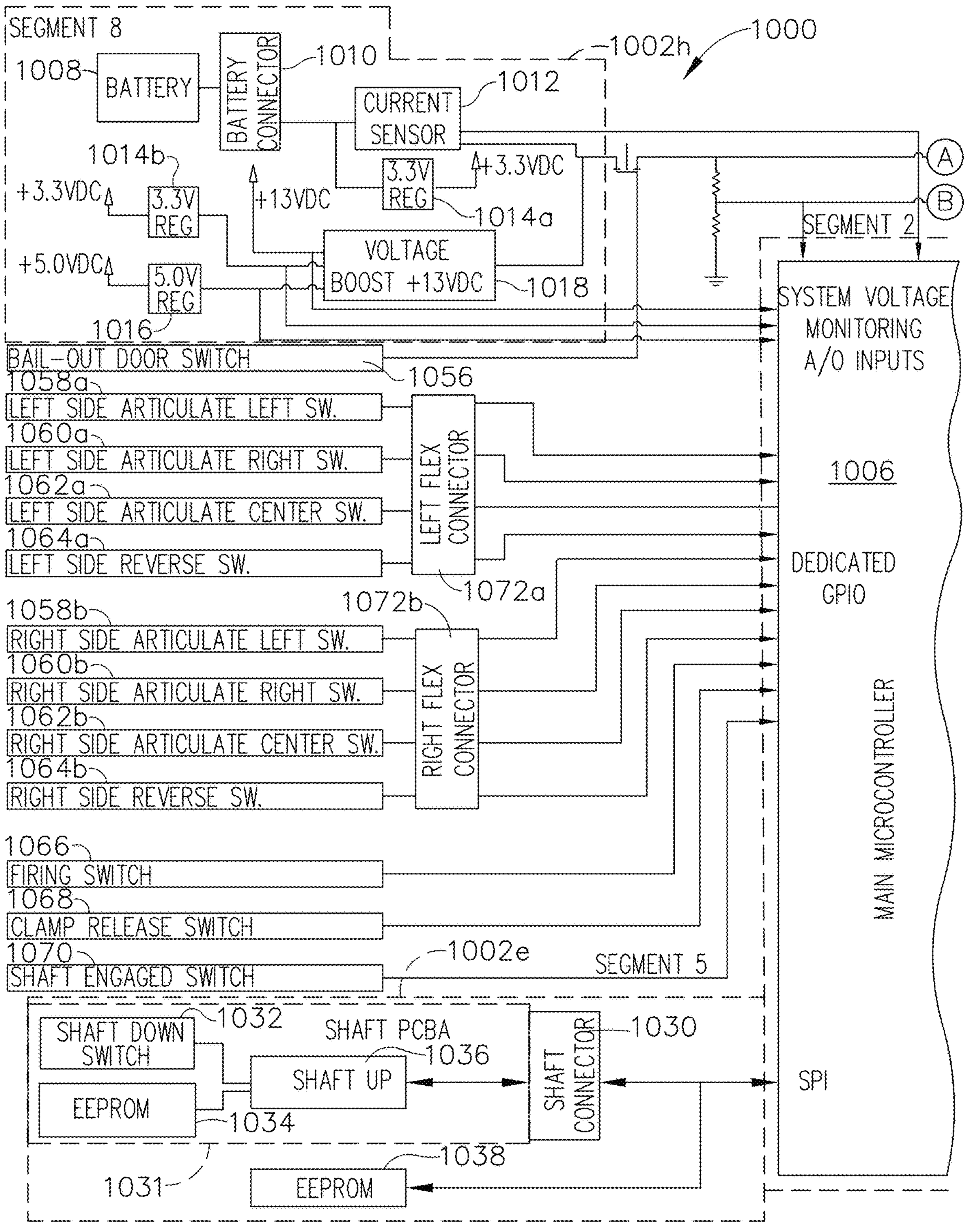
FIGS. 4A and 4B illustrate one embodiment of a segmented circuit comprising a plurality of circuit segments configured to control a powered surgical instrument.
Figure 4B:
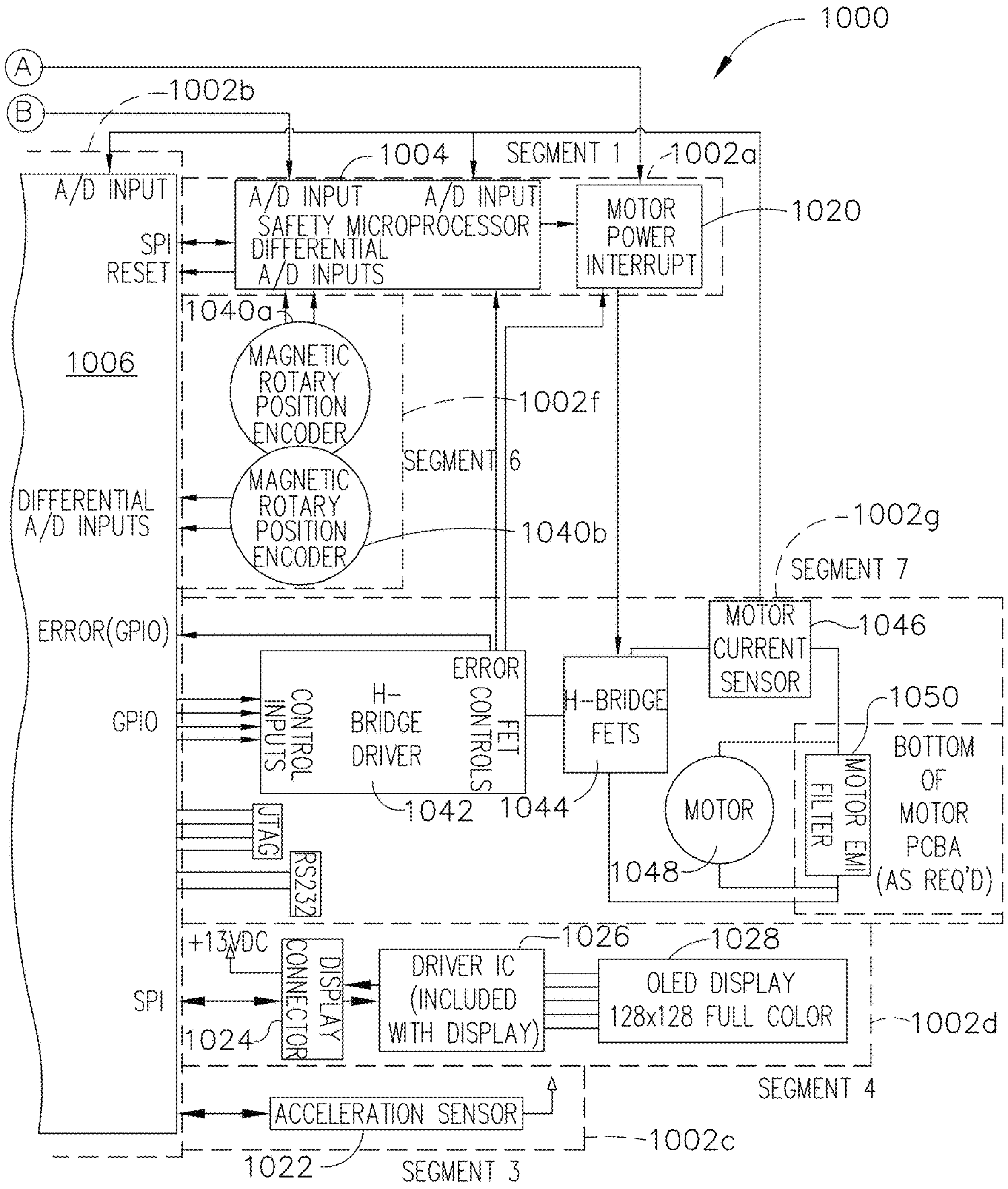

Having described a surgical instrument 2000 in general terms, the description now turns to a detailed description of various electrical/electronic component of the surgical instrument 2000. For expedience, any references hereinbelow to the surgical instrument 2000 should be construed to refer to the surgical instrument 2000 shown in connection with FIGS. 1-3B. Turning now to FIGS. 4A and 4B, where one embodiment of a segmented circuit 1000 comprising a plurality of circuit segments 1002*a*-1002*g* is illustrated. The segmented circuit 1000 comprising the plurality of circuit segments 1002*a*-1002*g* is configured to control a powered surgical instrument, such as, for example, the surgical instrument 2000 illustrated in FIGS. 1-3B, without limitation. The plurality of circuit segments 1002*a*-1002*g* is configured to control one or more operations of the powered surgical instrument 2000. A safety processor segment 1002*a* (Segment 1) comprises a safety processor 1004. A primary processor segment 1002*b* (Segment 2) comprises a primary processor 1006. The safety processor 1004 and/or the primary processor 1006 are configured to interact with one or more additional circuit segments 1002*c*-1002*g* to control operation of the powered surgical instrument 2000. The primary processor 1006 comprises a plurality of inputs coupled to, for example, one or more circuit segments 1002*c*-1002*g*, a battery 1008, and/or a plurality of switches 1058*a*-1070. The segmented circuit 1000 may be implemented by any suitable circuit, such as, for example, a printed circuit board assembly (PCBA) within the powered surgical instrument 2000. It should be understood that the term processor as used herein includes any microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one embodiment, the main processor 1006 may be any single core or multicore processor such as those known under the trade name ARM Cortex by Texas Instruments. In one embodiment, the safety processor 1004 may be a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one embodiment, the safety processor 1004 may be configured specifically for IEC 61508 and ISO 26262 safety critical applications, among others, to provide advanced integrated safety features while delivering scalable performance, connectivity, and memory options.

In certain instances, the main processor 1006 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. Other processors may be readily substituted and, accordingly, the present disclosure should not be limited in this context.

In one embodiment, the segmented circuit 1000 comprises an acceleration segment 1002*c* (Segment 3). The acceleration segment 1002*c* comprises an acceleration sensor 1022. The acceleration sensor 1022 may comprise, for example, an accelerometer. The acceleration sensor 1022 is configured to detect movement or acceleration of the powered surgical instrument 2000. In some embodiments, input from the acceleration sensor 1022 is used, for example, to transition to and from a sleep mode, identify an orientation of the powered surgical instrument, and/or identify when the surgical instrument has been dropped. In some embodiments, the acceleration segment 1002*c* is coupled to the safety processor 1004 and/or the primary processor 1006.

In one embodiment, the segmented circuit 1000 comprises a display segment 1002*d* (Segment 4). The display segment 1002*d* comprises a display connector 1024 coupled to the primary processor 1006. The display connector 1024 couples the primary processor 1006 to a display 1028 through one or more display driver integrated circuits 1026. The display driver integrated circuits 1026 may be integrated with the display 1028 and/or may be located separately from the display 1028. The display 1028 may comprise any suitable display, such as, for example, an organic light-emitting diode (OLED) display, a liquid crystal display (LCD), and/or any other suitable display. In some embodiments, the display segment 1002*d* is coupled to the safety processor 1004.

In some embodiments, the segmented circuit 1000 comprises a shaft segment 1002*e* (Segment 5). The shaft segment 1002*e* comprises one or more controls for a shaft 2004 coupled to the surgical instrument 2000 and/or one or more controls for an end effector 2006 coupled to the shaft 2004. The shaft segment 1002*e* comprises a shaft connector 1030 configured to couple the primary processor 1006 to a shaft PCBA 1031. The shaft PCBA 1031 comprises a first articulation switch 1036, a second articulation switch 1032, and a shaft PCBA electrically erasable programmable read-only memory (EEPROM) 1034. In some embodiments, the shaft PCBA EEPROM 1034 comprises one or more parameters, routines, and/or programs specific to the shaft 2004 and/or the shaft PCBA 1031. The shaft PCBA 1031 may be coupled to the shaft 2004 and/or integral with the surgical instrument 2000. In some embodiments, the shaft segment 1002*e* comprises a second shaft EEPROM 1038. The second shaft EEPROM 1038 comprises a plurality of algorithms, routines, parameters, and/or other data corresponding to one or more shafts 2004 and/or end effectors 2006 which may be interfaced with the powered surgical instrument 2000.

In some embodiments, the segmented circuit 1000 comprises a position encoder segment 1002*f* (Segment 6). The position encoder segment 1002*f* comprises one or more magnetic rotary position encoders 1040*a*-1040*b*. The one or more magnetic rotary position encoders 1040*a*-1040*b* are configured to identify the rotational position of a motor 1048, a shaft 2004, and/or an end effector 2006 of the surgical instrument 2000. In some embodiments, the magnetic rotary position encoders 1040*a*-1040*b* may be coupled to the safety processor 1004 and/or the primary processor 1006.

In some embodiments, the segmented circuit 1000 comprises a motor segment 1002*g* (Segment 7). The motor segment 1002*g* comprises a motor 1048 configured to control one or more movements of the powered surgical instrument 2000. The motor 1048 is coupled to the primary processor 1006 by an H-Bridge driver 1042 and one or more H-bridge field-effect transistors (FETs) 1044. The H-bridge FETs 1044 are coupled to the safety processor 1004. A motor current sensor 1046 is coupled in series with the motor 1048 to measure the current draw of the motor 1048. The motor current sensor 1046 is in signal communication with the primary processor 1006 and/or the safety processor 1004. In some embodiments, the motor 1048 is coupled to a motor electromagnetic interference (EMI) filter 1050.

The segmented circuit 1000 comprises a power segment 1002*h* (Segment 8). A battery 1008 is coupled to the safety processor 1004, the primary processor 1006, and one or more of the additional circuit segments 1002*c*-1002*g*. The battery 1008 is coupled to the segmented circuit 1000 by a battery connector 1010 and a current sensor 1012. The current sensor 1012 is configured to measure the total current draw of the segmented circuit 1000. In some embodiments, one or more voltage converters 1014*a*, 1014*b*, 1016 are configured to provide predetermined voltage values to one or more circuit segments 1002*a*-1002*g*. For example, in some embodiments, the segmented circuit 1000 may comprise 3.3V voltage converters 1014*a*-1014*b* and/or 5V voltage converters 1016. A boost converter 1018 is configured to provide a boost voltage up to a predetermined amount, such as, for example, up to 13V. The boost converter 1018 is configured to provide additional voltage and/or current during power intensive operations and prevent brownout or low-power conditions.

In some embodiments, the safety segment 1002*a* comprises a motor power interrupt 1020. The motor power interrupt 1020 is coupled between the power segment 1002*h* and the motor segment 1002*g*. The safety segment 1002*a* is configured to interrupt power to the motor segment 1002*g* when an error or fault condition is detected by the safety processor 1004 and/or the primary processor 1006 as discussed in more detail herein. Although the circuit segments 1002*a*-1002*g* are illustrated with all components of the circuit segments 1002*a*-1002*h* located in physical proximity, one skilled in the art will recognize that a circuit segment 1002*a*-1002*h* may comprise components physically and/or electrically separate from other components of the same circuit segment 1002*a*-1002*g*. In some embodiments, one or more components may be shared between two or more circuit segments 1002*a*-1002*g*.

In some embodiments, a plurality of switches 1056-1070 are coupled to the safety processor 1004 and/or the primary processor 1006. The plurality of switches 1056-1070 may be configured to control one or more operations of the surgical instrument 2000, control one or more operations of the segmented circuit 1100, and/or indicate a status of the surgical instrument 2000. For example, a bail-out door switch 1056 is configured to indicate the status of a bail-out door. A plurality of articulation switches, such as, for example, a left side articulation left switch 1058*a*, a left side articulation right switch 1060*a*, a left side articulation center switch 1062*a*, a right side articulation left switch 1058*b*, a right side articulation right switch 1060*b*, and a right side articulation center switch 1062*b* are configured to control articulation of a shaft 2004 and/or an end effector 2006. A left side reverse switch 1064*a* and a right side reverse switch 1064*b* are coupled to the primary processor 1006. In some embodiments, the left side switches comprising the left side articulation left switch 1058*a*, the left side articulation right switch 1060*a*, the left side articulation center switch 1062*a*, and the left side reverse switch 1064*a* are coupled to the primary processor 1006 by a left flex connector 1072*a*. The right side switches comprising the right side articulation left switch 1058*b*, the right side articulation right switch 1060*b*, the right side articulation center switch 1062*b*, and the right side reverse switch 1064*b* are coupled to the primary processor 1006 by a right flex connector 1072*b*. In some embodiments, a firing switch 1066, a clamp release switch 1068, and a shaft engaged switch 1070 are coupled to the primary processor 1006.

The plurality of switches 1056-1070 may comprise, for example, a plurality of handle controls mounted to a handle of the surgical instrument 2000, a plurality of indicator switches, and/or any combination thereof. In various embodiments, the plurality of switches 1056-1070 allow a surgeon to manipulate the surgical instrument, provide feedback to the segmented circuit 1000 regarding the position and/or operation of the surgical instrument, and/or indicate unsafe operation of the surgical instrument 2000. In some embodiments, additional or fewer switches may be coupled to the segmented circuit 1000, one or more of the switches 1056-1070 may be combined into a single switch, and/or expanded to multiple switches. For example, in one embodiment, one or more of the left side and/or right side articulation switches 1058*a*-1064*b* may be combined into a single multi-position switch.

Figure 5A:
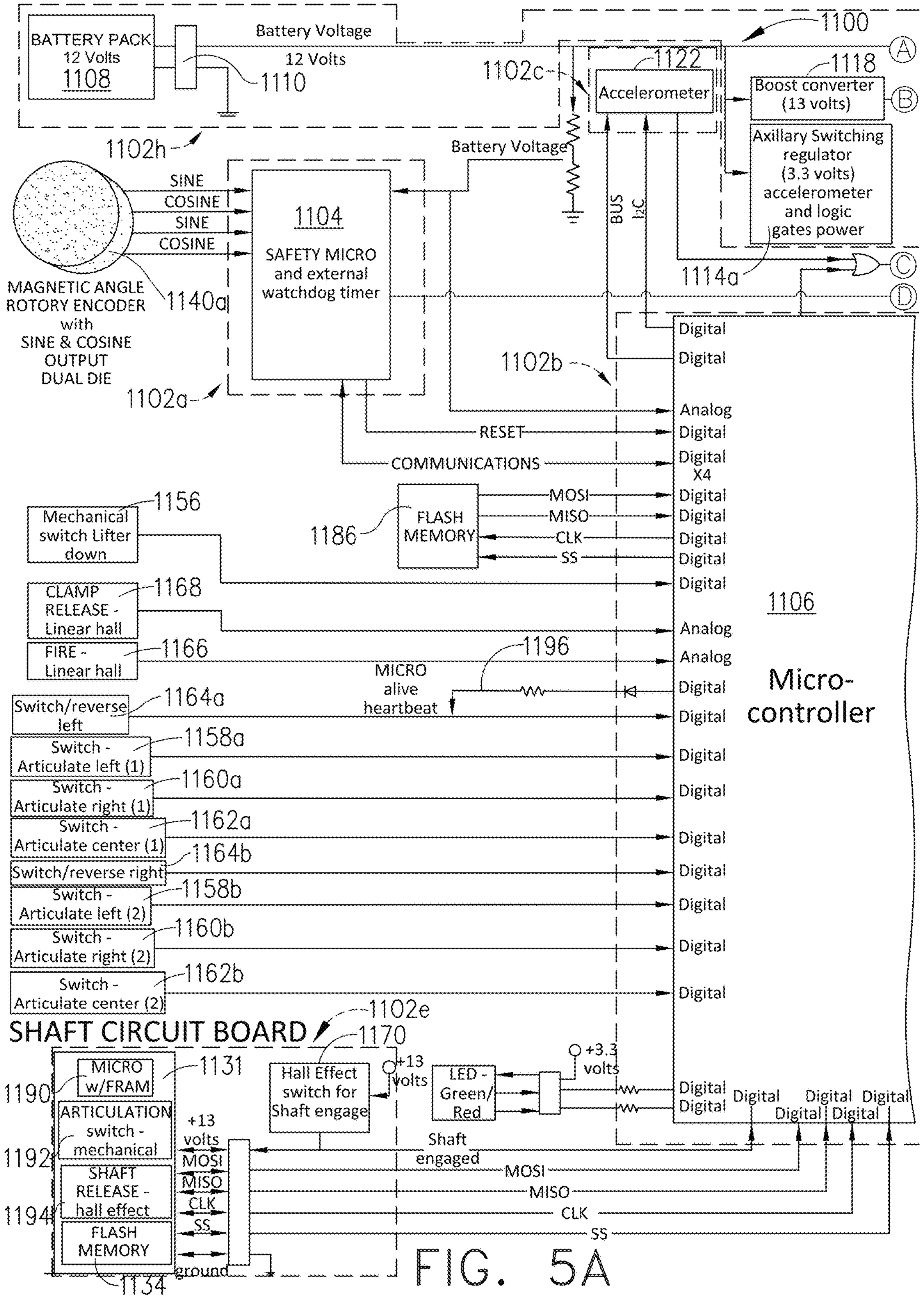
FIGS. 5A and 5B illustrate a segmented circuit comprising a safety processor configured to implement a watchdog function.
Figure 5B:
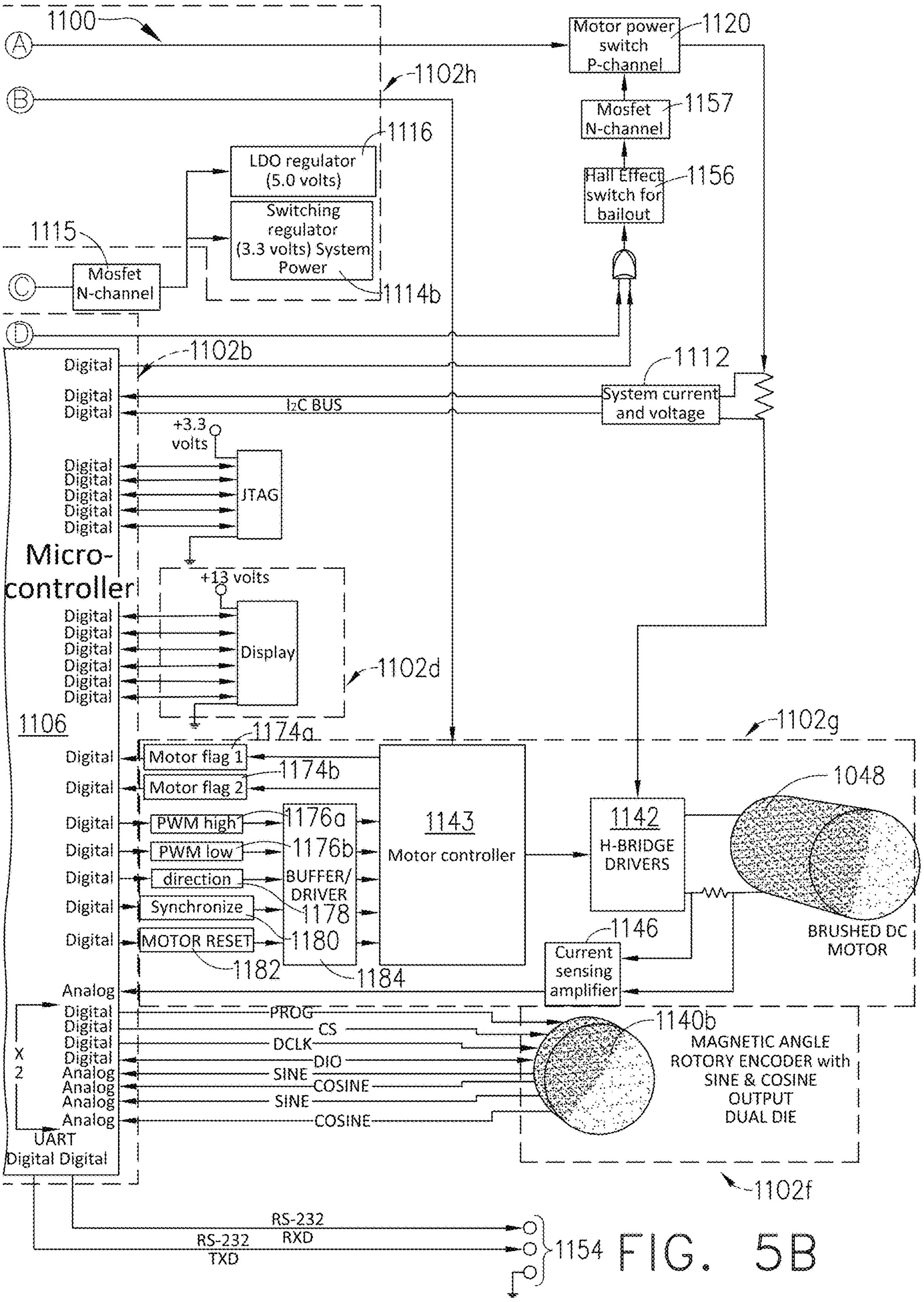

FIGS. 5A and 5B illustrate a segmented circuit 1100 comprising one embodiment of a safety processor 1104 configured to implement a watchdog function, among other safety operations. The safety processor 1004 and the primary processor 1106 of the segmented circuit 1100 are in signal communication. A plurality of circuit segments 1102*c*-1102*h* are coupled to the primary processor 1106 and are configured to control one or more operations of a surgical instrument, such as, for example, the surgical instrument 2000 illustrated in FIGS. 1-3B. For example, in the illustrated embodiment, the segmented circuit 1100 comprises an acceleration segment 1102*c*, a display segment 1102*d*, a shaft segment 1102*e*, an encoder segment 1102*f*, a motor segment 1102*g*, and a power segment 1102*h*. Each of the circuit segments 1102*c*-1102*g* may be coupled to the safety processor 1104 and/or the primary processor 1106. The primary processor is also coupled to a flash memory 1186. A microprocessor alive heartbeat signal is provided at output 1196.

The acceleration segment 1102*c* comprises an accelerometer 1122 configured to monitor movement of the surgical instrument 2000. In various embodiments, the accelerometer 1122 may be a single, double, or triple axis accelerometer. The accelerometer 1122 may be employed to measures proper acceleration that is not necessarily the coordinate acceleration (rate of change of velocity). Instead, the accelerometer sees the acceleration associated with the phenomenon of weight experienced by a test mass at rest in the frame of reference of the accelerometer 1122. For example, the accelerometer 1122 at rest on the surface of the earth will measure an acceleration $g=9.8\ m/s^2$ (gravity) straight upwards, due to its weight. Another type of acceleration that accelerometer 1122 can measure is g-force acceleration. In various other embodiments, the accelerometer 1122 may comprise a single, double, or triple axis accelerometer. Further, the acceleration segment 1102*c* may comprise one or more inertial sensors to detect and measure acceleration, tilt, shock, vibration, rotation, and multiple degrees-of-freedom (DoF). A suitable inertial sensor may comprise an accelerometer (single, double, or triple axis), a magnetometer to measure a magnetic field in space such as the earth's magnetic field, and/or a gyroscope to measure angular velocity.

The display segment 1102*d* comprises a display embedded in the surgical instrument 2000, such as, for example, an OLED display. In certain embodiments, the surgical instrument 2000 may comprise an output device which may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In some aspects, the output device may comprise a display which may be included in the handle assembly 2002, as illustrated in FIG. 1. The shaft assembly controller and/or the power management controller can provide feedback to a user of the surgical instrument 2000 through the output device. An interface can be configured to connect the shaft assembly controller and/or the power management controller to the output device.

The shaft segment 1102*e* comprises a shaft circuit board 1131, such as, for example, a shaft PCB, configured to control one or more operations of a shaft 2004 and/or an end effector 2006 coupled to the shaft 2004 and a Hall effect switch 1170 to indicate shaft engagement. The shaft circuit board 1131 also includes a low-power microprocessor 1190 with ferroelectric random access memory (FRAM) technology, a mechanical articulation switch 1192, a shaft release Hall Effect switch 1194, and flash memory 1134. The encoder segment 1102*f* comprises a plurality of motor encoders 1140*a*, 1140*b* configured to provide rotational position information of a motor 1048, the shaft 2004, and/or the end effector 2006.

The motor segment 1102*g* comprises a motor 1048, such as, for example, a brushed DC motor. The motor 1048 is coupled to the primary processor 1106 through a plurality of H-bridge drivers 1142 and a motor controller 1143. The motor controller 1143 controls a first motor flag 1174*a* and a second motor flag 1174*b* to indicate the status and position of the motor 1048 to the primary processor 1106. The primary processor 1106 provides a pulse-width modulation (PWM) high signal 1176*a*, a PWM low signal 1176*b*, a direction signal 1178, a synchronize signal 1180, and a motor reset signal 1182 to the motor controller 1143 through a buffer 1184. The power segment 1102*h* is configured to provide a segment voltage to each of the circuit segments 1102*a*-1102*g*.

In one embodiment, the safety processor 1104 is configured to implement a watchdog function with respect to one or more circuit segments 1102*c*-1102*h*, such as, for example, the motor segment 1102*g*. In this regards, the safety processor 1104 employs the watchdog function to detect and recover from malfunctions of the primary processor 10006. During normal operation, the safety processor 1104 monitors for hardware faults or program errors of the primary processor 1104 and to initiate corrective action or actions. The corrective actions may include placing the primary processor 10006 in a safe state and restoring normal system operation. In one embodiment, the safety processor 1104 is coupled to at least a first sensor. The first sensor measures a first property of the surgical instrument 2000. In some embodiments, the safety processor 1104 is configured to compare the measured property of the surgical instrument 2000 to a predetermined value. For example, in one embodiment, a motor sensor 1140*a* is coupled to the safety processor 1104. The motor sensor 1140*a* provides motor speed and position information to the safety processor 1104. The safety processor 1104 monitors the motor sensor 1140*a* and compares the value to a maximum speed and/or position value and prevents operation of the motor 1048 above the predetermined values. In some embodiments, the predetermined values are calculated based on real-time speed and/or position of the motor 1048, calculated from values supplied by a second motor sensor 1140*b* in communication with the primary processor 1106, and/or provided to the safety processor 1104 from, for example, a memory module coupled to the safety processor 1104.

In some embodiments, a second sensor is coupled to the primary processor 1106. The second sensor is configured to measure the first physical property. The safety processor 1104 and the primary processor 1106 are configured to provide a signal indicative of the value of the first sensor and the second sensor respectively. When either the safety processor 1104 or the primary processor 1106 indicates a value outside of an acceptable range, the segmented circuit 1100 prevents operation of at least one of the circuit segments 1102*c*-1102*h*, such as, for example, the motor segment 1102*g*. For example, in the embodiment illustrated in FIGS. 5A and 5B, the safety processor 1104 is coupled to a first motor position sensor 1140*a* and the primary processor 1106 is coupled to a second motor position sensor 1140*b*. The motor position sensors 1140*a*, 1140*b* may comprise any suitable motor position sensor, such as, for example, a magnetic angle rotary input comprising a sine and cosine output. The motor position sensors 1140*a*, 1140*b* provide respective signals to the safety processor 1104 and the primary processor 1106 indicative of the position of the motor 1048.

The safety processor 1104 and the primary processor 1106 generate an activation signal when the values of the first motor sensor 1140*a* and the second motor sensor 1140*b* are within a predetermined range. When either the primary processor 1106 or the safety processor 1104 to detect a value outside of the predetermined range, the activation signal is terminated and operation of at least one circuit segment 1102*c*-1102*h*, such as, for example, the motor segment 1102*g*, is interrupted and/or prevented. For example, in some embodiments, the activation signal from the primary processor 1106 and the activation signal from the safety processor 1104 are coupled to an AND gate. The AND gate is coupled to a motor power switch 1120. The AND gate maintains the motor power switch 1120 in a closed, or on, position when the activation signal from both the safety processor 1104 and the primary processor 1106 are high, indicating a value of the motor sensors 1140*a*, 1140*b* within the predetermined range. When either of the motor sensors 1140*a*, 1140*b* detect a value outside of the predetermined range, the activation signal from that motor sensor 1140*a*, 1140*b* is set low, and the output of the AND gate is set low, opening the motor power switch 1120. In some embodiments, the value of the first sensor 1140*a* and the second sensor 1140*b* is compared, for example, by the safety processor 1104 and/or the primary processor 1106. When the values of the first sensor and the second sensor are different, the safety processor 1104 and/or the primary processor 1106 may prevent operation of the motor segment 1102*g*.

In some embodiments, the safety processor 1104 receives a signal indicative of the value of the second sensor 1140*b* and compares the second sensor value to the first sensor value. For example, in one embodiment, the safety processor 1104 is coupled directly to a first motor sensor 1140*a*. A second motor sensor 1140*b* is coupled to a primary processor 1106, which provides the second motor sensor 1140*b* value to the safety processor 1104, and/or coupled directly to the safety processor 1104. The safety processor 1104 compares the value of the first motor sensor 1140 to the value of the second motor sensor 1140*b*. When the safety processor 1104 detects a mismatch between the first motor sensor 1140*a* and the second motor sensor 1140*b*, the safety processor 1104 may interrupt operation of the motor segment 1102*g*, for example, by cutting power to the motor segment 1102*g*.

In some embodiments, the safety processor 1104 and/or the primary processor 1106 is coupled to a first sensor 1140*a* configured to measure a first property of a surgical instrument and a second sensor 1140*b* configured to measure a second property of the surgical instrument. The first property and the second property comprise a predetermined relationship when the surgical instrument is operating normally. The safety processor 1104 monitors the first property and the second property. When a value of the first property and/or the second property inconsistent with the predetermined relationship is detected, a fault occurs. When a fault occurs, the safety processor 1104 takes at least one action, such as, for example, preventing operation of at least one of the circuit segments, executing a predetermined operation, and/or resetting the primary processor 1106. For example, the safety processor 1104 may open the motor power switch 1120 to cut power to the motor circuit segment 1102*g* when a fault is detected.

Figure 6:
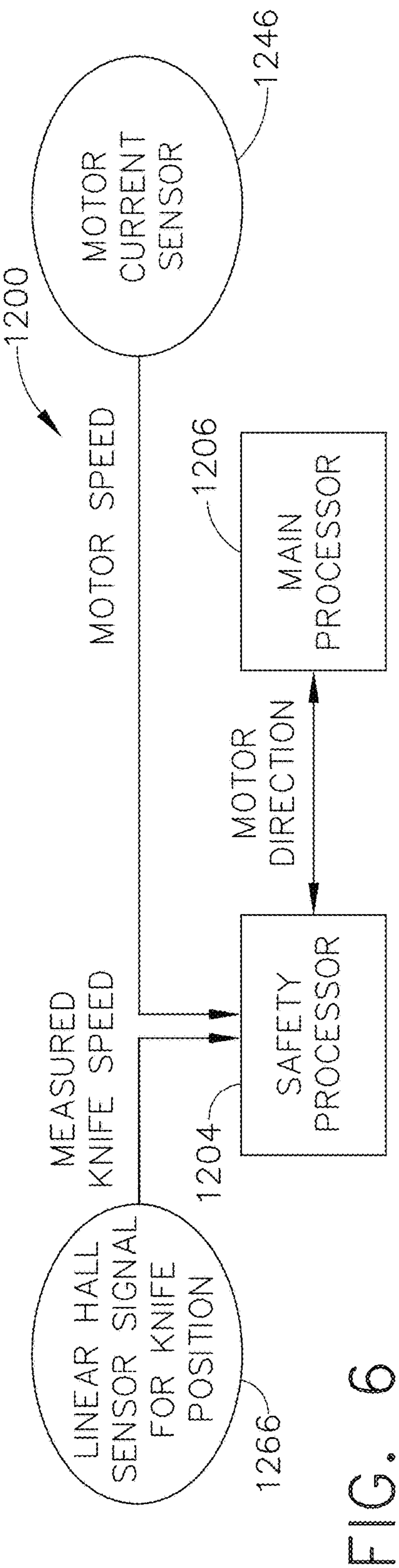
FIG. 6 illustrates a block diagram of one embodiment of a segmented circuit comprising a safety processor configured to monitor and compare a first property and a second property of a surgical instrument.

FIG. 6 illustrates a block diagram of one embodiment of a segmented circuit 1200 comprising a safety processor 1204 configured to monitor and compare a first property and a second property of a surgical instrument, such as, for example, the surgical instrument 2000 illustrated in FIGS. 1-3B. The safety processor 1204 is coupled to a first sensor 1246 and a second sensor 1266. The first sensor 1246 is configured to monitor a first physical property of the surgical instrument 2000. The second sensor 1266 is configured to monitor a second physical property of the surgical instrument 2000. The first and second properties comprise a predetermined relationship when the surgical instrument 2000 is operating normally. For example, in one embodiment, the first sensor 1246 comprises a motor current sensor configured to monitor the current draw of a motor from a power source. The motor current draw may be indicative of the speed of the motor. The second sensor comprises a linear hall sensor configured to monitor the position of a cutting member within an end effector, for example, an end effector 2006 coupled to the surgical instrument 2000. The position of the cutting member is used to calculate a cutting member speed within the end effector 2006. The cutting member speed has a predetermined relationship with the speed of the motor when the surgical instrument 2000 is operating normally.

The safety processor 1204 provides a signal to the main processor 1206 indicating that the first sensor 1246 and the second sensor 1266 are producing values consistent with the predetermined relationship. When the safety processor 1204 detects a value of the first sensor 1246 and/or the second sensor 1266 inconsistent with the predetermined relationship, the safety processor 1206 indicates an unsafe condition to the primary processor 1206. The primary processor 1206 interrupts and/or prevents operation of at least one circuit segment. In some embodiments, the safety processor 1204 is coupled directly to a switch configured to control operation of one or more circuit segments. For example, with reference to FIGS. 5A and 5B, in one embodiment, the safety processor 1104 is coupled directly to a motor power switch 1120. The safety processor 1104 opens the motor power switch 1120 to prevent operation of the motor segment 1102*g* when a fault is detected.

Referring back to FIGS. 5A and 5B, in one embodiment, the safety processor 1104 is configured to execute an independent control algorithm. In operation, the safety processor 1104 monitors the segmented circuit 1100 and is configured to control and/or override signals from other circuit components, such as, for example, the primary processor 1106, independently. The safety processor 1104 may execute a preprogrammed algorithm and/or may be updated or programmed on the fly during operation based on one or more actions and/or positions of the surgical instrument 2000. For example, in one embodiment, the safety processor 1104 is reprogrammed with new parameters and/or safety algorithms each time a new shaft and/or end effector is coupled to the surgical instrument 2000. In some embodiments, one or more safety values stored by the safety processor 1104 are duplicated by the primary processor 1106. Two-way error detection is performed to ensure values and/or parameters stored by either of the processors 1104, 1106 are correct.

In some embodiments, the safety processor 1104 and the primary processor 1106 implement a redundant safety check. The safety processor 1104 and the primary processor 1106 provide periodic signals indicating normal operation. For example, during operation, the safety processor 1104 may indicate to the primary processor 1106 that the safety processor 1104 is executing code and operating normally. The primary processor 1106 may, likewise, indicate to the safety processor 1104 that the primary processor 1106 is executing code and operating normally. In some embodiments, communication between the safety processor 1104 and the primary processor 1106 occurs at a predetermined interval. The predetermined interval may be constant or may be variable based on the circuit state and/or operation of the surgical instrument 2000.

Figure 7:
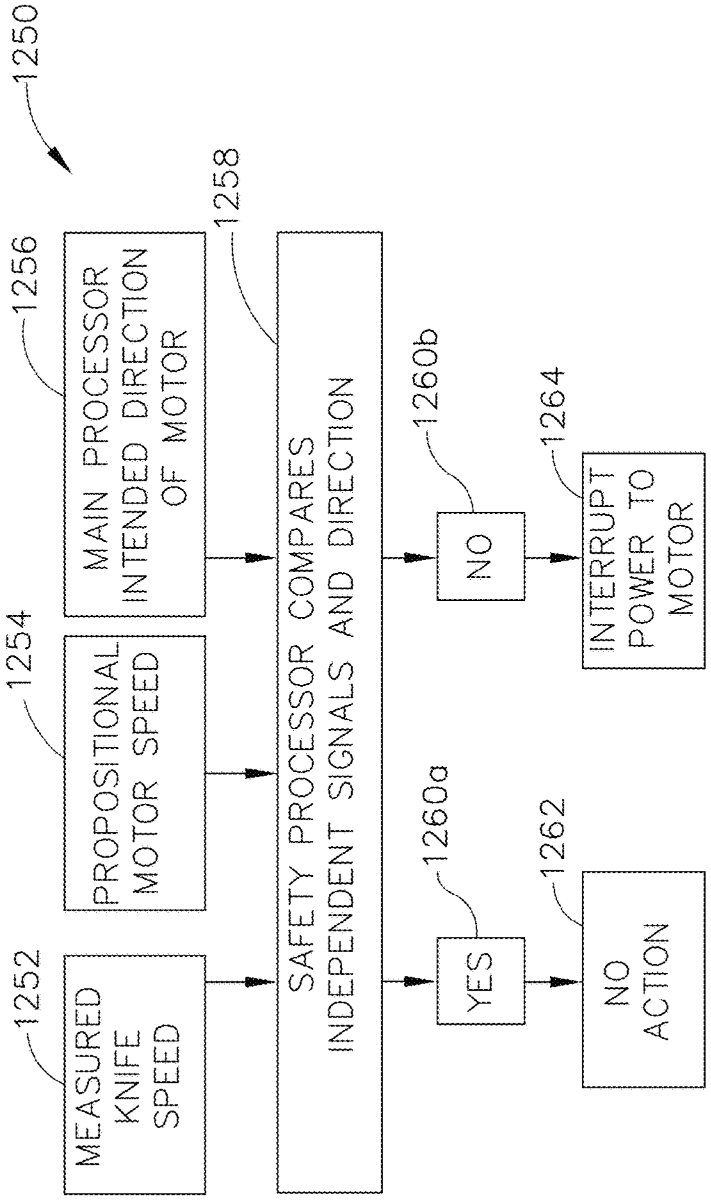
FIG. 7 illustrates a block diagram illustrating a safety process configured to be implemented by a safety processor.

FIG. 7 is a block diagram illustrating a safety process 1250 configured to be implemented by a safety processor, such as, for example, the safety process 1104 illustrated in FIGS. 5A and 5B. In one embodiment, values corresponding to a plurality of properties of a surgical instrument 2000 are provided to the safety processor 1104. The plurality of properties is monitored by a plurality of independent sensors and/or systems. For example, in the illustrated embodiment, a measured cutting member speed 1252, a propositional motor speed 1254, and an intended direction of motor signal 1256 are provided to a safety processor 1104. The cutting member speed 1252 and the propositional motor speed 1254 may be provided by independent sensors, such as, for example, a linear hall sensor and a current sensor respectively. The intended direction of motor signal 1256 may be provided by a primary processor, for example, the primary processor 1106 illustrated in FIGS. 5A and 5B. The safety processor 1104 compares 1258 the plurality of properties and determines when the properties are consistent with a predetermined relationship. When the plurality of properties comprises values consistent with the predetermined relationship 1260*a*, no action is taken 1262. When the plurality of properties comprises values inconsistent with the predetermined relationship 1260*b*, the safety processor 1104 executes one or more actions, such as, for example, blocking a function, executing a function, and/or resetting a processor. For example, in the process 1250 illustrated in FIG. 7, the safety processor 1104 interrupts operation of one or more circuit segments, such as, for example, by interrupting power 1264 to a motor segment.

Referring back to FIGS. 5A and 5B, the segmented circuit 1100 comprises a plurality of switches 1156-1170 configured to control one or more operations of the surgical instrument 2000. For example, in the illustrated embodiment, the segmented circuit 1100 comprises a clamp release switch 1168, a firing trigger 1166, and a plurality of switches 1158*a*-1164*b* configured to control articulation of a shaft 2004 and/or end effector 2006 coupled to the surgical instrument 2000. The clamp release switch 1168, the fire trigger 1166, and the plurality of articulation switches 1158*a*-1164*b* may comprise analog and/or digital switches. In particular, switch 1156 indicates the mechanical switch lifter down position, switches 1158*a*, 1158*b* indicate articulate left (1) and (2), switch 1160*a*, 1160*b* indicate articulate right (1) and (2), switches 1162*a*, 1162*b* indicate articulate center (1) and (2), and switches 1164*a*, 1164*b* indicate reverse/left and reverse/right.

Figure 8:
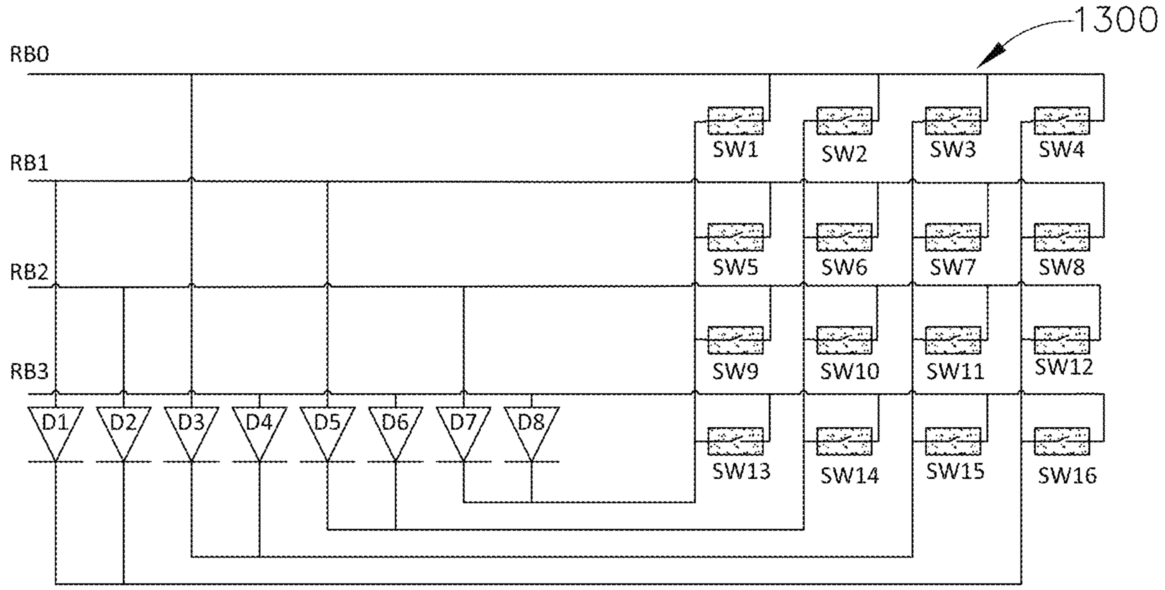
FIG. 8 illustrates one embodiment of a four by four switch bank comprising four input/output pins.

For example, FIG. 8 illustrates one embodiment of a switch bank 1300 comprising a plurality of switches SW1-SW16 configured to control one or more operations of a surgical instrument. The switch bank 1300 may be coupled to a primary processor, such as, for example, the primary processor 1106. In some embodiments, one or more diodes D1-D8 are coupled to the plurality of switches SW1-SW16. Any suitable mechanical, electromechanical, or solid state switches may be employed to implement the plurality of switches 1156-1170, in any combination. For example, the switches 1156-1170 may limit switches operated by the motion of components associated with the surgical instrument 2000 or the presence of an object. Such switches may be employed to control various functions associated with the surgical instrument 2000. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches 1156-1170 may be solid state switches that operate under the influence of a magnetic field such as Hall-effect devices, magneto-resistive (MR) devices, giant magneto-resistive (GMR) devices, magnetometers, among others. In other implementations, the switches 1156-1170 may be solid state switches that operate under the influence of light, such as optical sensors, infrared sensors, ultraviolet sensors, among others. Still, the switches 1156-1170 may be solid state devices such as transistors (e.g., FET, Junction-FET, metal-oxide semiconductor-FET (MOSFET), bipolar, and the like). Other switches may include wireless switches, ultrasonic switches, accelerometers, inertial sensors, among others.

Figure 9:
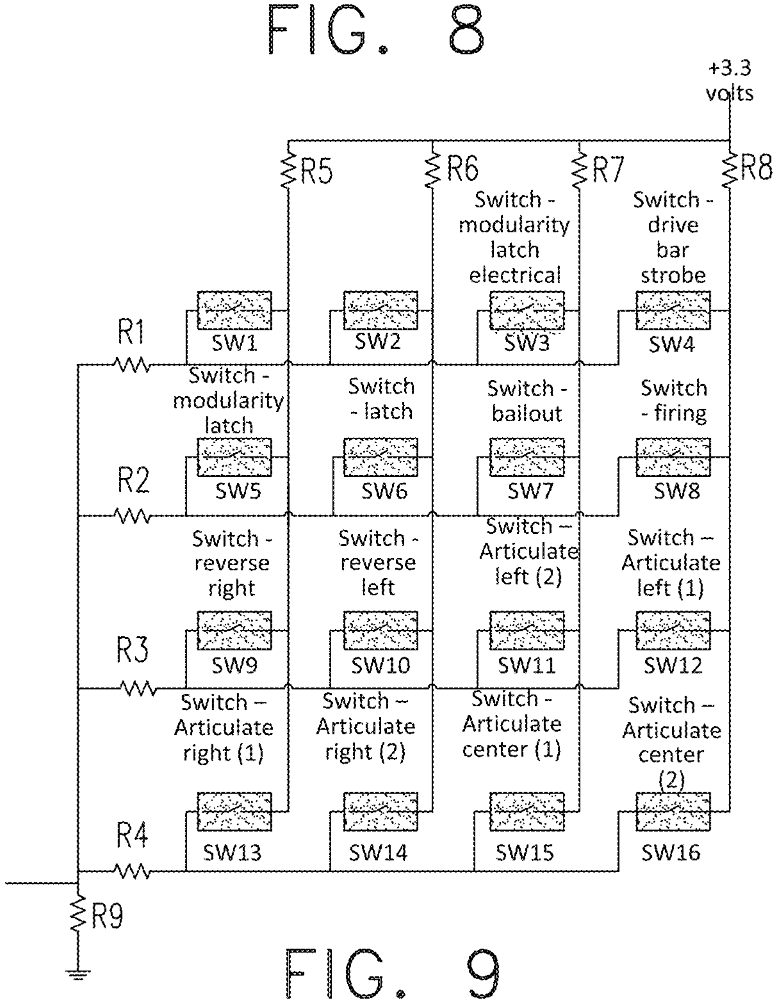
FIG. 9 illustrates one embodiment of a four by four bank circuit comprising one input/output pin.

FIG. 9 illustrates one embodiment of a switch bank 1350 comprising a plurality of switches. In various embodiments, one or more switches are configured to control one or more operations of a surgical instrument, such as, for example, the surgical instrument 2000 illustrated in FIGS. 1-3B. A plurality of articulation switches SW1-SW16 is configured to control articulation of a shaft 2004 and/or an end effector 2006 coupled to the surgical instrument 2000. A firing trigger 1366 is configured to fire the surgical instrument 2000, for example, to deploy a plurality of staples, translate a cutting member within the end effector 2006, and/or deliver electrosurgical energy to the end effector 2006. In some embodiments, the switch bank 1350 comprises one or more safety switches configured to prevent operation of the surgical instrument 2000. For example, a bailout switch 1356 is coupled to a bailout door and prevents operation of the surgical instrument 2000 when the bailout door is in an open position.

Figure 10A:
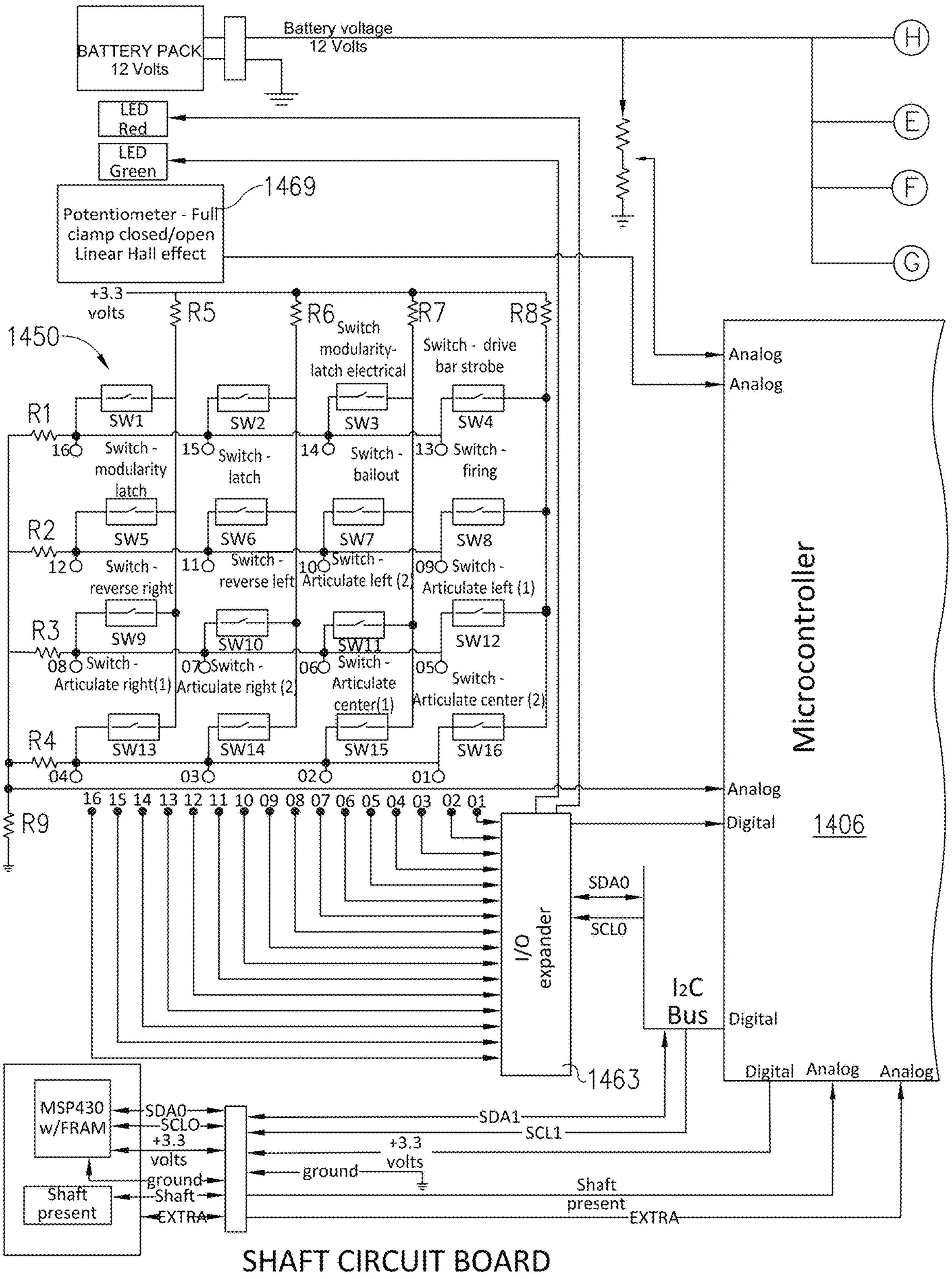
FIGS. 10A and 10B illustrate one embodiment of a segmented circuit comprising a four by four switch bank coupled to a primary processor.
Figure 10B:
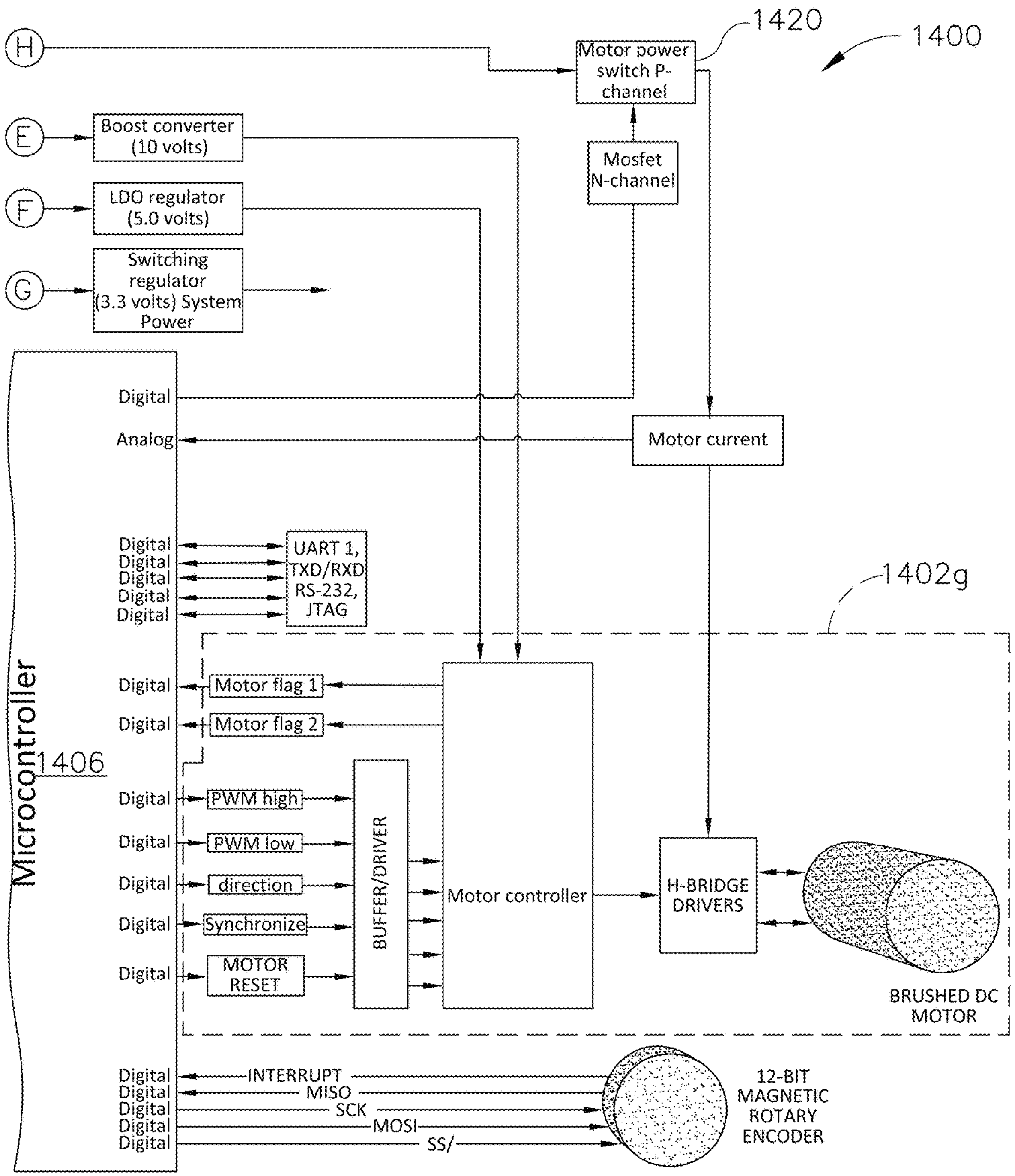

FIGS. 10A and 10B illustrate one embodiment of a segmented circuit 1400 comprising a switch bank 1450 coupled to the primary processor 1406. The switch bank 1450 is similar to the switch bank 1350 illustrated in FIG. 9. The switch bank 1450 comprises a plurality of switches SW1-SW16 configured to control one or more operations of a surgical instrument, such as, for example, the surgical instrument 2000 illustrated in FIGS. 1-3B. The switch bank 1450 is coupled to an analog input of the primary processor 1406. Each of the switches within the switch bank 1450 is further coupled to an input/output expander 1463 coupled to a digital input of the primary processor 1406. The primary processor 1406 receives input from the switch bank 1450 and controls one or more additional segments of the segmented circuit 1400, such as, for example, a motor segment 1402*g* in response to manipulation of one or more switches of the switch bank 1450.

In some embodiments, a potentiometer 1469 is coupled to the primary processor 1406 to provide a signal indicative of a clamp position of an end effector 2006 coupled to the surgical instrument 2000. The potentiometer 1469 may replace and/or supplement a safety processor (not shown) by providing a signal indicative of a clamp open/closed position used by the primary processor 1106 to control operation of one or more circuit segments, such as, for example, the motor segment 1102*g*. For example, when the potentiometer 1469 indicates that the end effector is in a fully clamped position and/or a fully open position, the primary processor 1406 may open the motor power switch 1420 and prevent further operation of the motor segment 1402*g* in a specific direction. In some embodiments, the primary processor 1406 controls the current delivered to the motor segment 1402*g* in response to a signal received from the potentiometer 1469. For example, the primary processor 1406 may limit the energy that can be delivered to the motor segment 1402*g* when the potentiometer 1469 indicates that the end effector is closed beyond a predetermined position.

Referring back to FIGS. 5A and 5B, the segmented circuit 1100 comprises an acceleration segment 1102*c*. The acceleration segment comprises an accelerometer 1122. The accelerometer 1122 may be coupled to the safety processor 1104 and/or the primary processor 1106. The accelerometer 1122 is configured to monitor movement of the surgical instrument 2000. The accelerometer 1122 is configured to generate one or more signals indicative of movement in one or more directions. For example, in some embodiments, the accelerometer 1122 is configured to monitor movement of the surgical instrument 2000 in three directions. In other embodiments, the acceleration segment 1102*c* comprises a plurality of accelerometers 1122, each configured to monitor movement in a signal direction.

In some embodiments, the accelerometer 1122 is configured to initiate a transition to and/or from a sleep mode, e.g., between sleep-mode and wake-up mode and vice versa. Sleep mode may comprise a low-power mode in which one or more of the circuit segments 1102*a*-1102*g* are deactivated or placed in a low-power state. For example, in one embodiment, the accelerometer 1122 remains active in sleep mode and the safety processor 1104 is placed into a low-power mode in which the safety processor 1104 monitors the accelerometer 1122, but otherwise does not perform any functions. The remaining circuit segments 1102*b*-1102*g* are powered off. In various embodiments, the primary processor 1104 and/or the safety processor 1106 are configured to monitor the accelerometer 1122 and transition the segmented circuit 1100 to sleep mode, for example, when no movement is detected within a predetermined time period. Although described in connection with the safety processor 1104 monitoring the accelerometer 1122, the sleep-mode/wake-up mode may be implemented by the safety processor 1104 monitoring any of the sensors, switches, or other indicators associated with the surgical instrument 2000 as described herein. For example, the safety processor 1104 may monitor an inertial sensor, or a one or more switches.

In some embodiments, the segmented circuit 1100 transitions to sleep mode after a predetermined period of inactivity. A timer is in signal communication with the safety processor 1104 and/or the primary processor 1106. The timer may be integral with the safety processor 1104, the primary processor 1106, and/or may be a separate circuit component. The timer is configured to monitor a time period since a last movement of the surgical instrument 2000 was detected by the accelerometer 1122. When the counter exceeds a predetermined threshold, the safety processor 1104 and/or the primary processor 1106 transitions the segmented circuit 1100 into sleep mode. In some embodiments, the timer is reset each time the accelerometer 1122 detects movement.

In some embodiments, all circuit segments except the accelerometer 1122, or other designated sensors and/or switches, and the safety processor 1104 are deactivated when in sleep mode. The safety processor 1104 monitors the accelerometer 1122, or other designated sensors and/or switches. When the accelerometer 1122 indicates movement of the surgical instrument 2000, the safety processor 1104 initiates a transition from sleep mode to operational mode. In operational mode, all of the circuit segments 1102*a*-1102*h* are fully energized and the surgical instrument 2000 is ready for use. In some embodiments, the safety processor 1104 transitions the segmented circuit 1100 to the operational mode by providing a signal to the primary processor 1106 to transition the primary processor 1106 from sleep mode to a full power mode. The primary processor 1106, then transitions each of the remaining circuit segments 1102*d*-1102*h* to operational mode.

The transition to and/or from sleep mode may comprise a plurality of stages. For example, in one embodiment, the segmented circuit 1100 transitions from the operational mode to the sleep mode in four stages. The first stage is initiated after the accelerometer 1122 has not detected movement of the surgical instrument for a first predetermined time period. After the first predetermined time period the segmented circuit 1100 dims a backlight of the display segment 1102*d*. When no movement is detected within a second predetermined period, the safety processor 1104 transitions to a second stage, in which the backlight of the display segment 1102*d* is turned off. When no movement is detected within a third predetermined time period, the safety processor 1104 transitions to a third stage, in which the polling rate of the accelerometer 1122 is reduced. When no movement is detected within a fourth predetermined time period, the display segment 1102*d* is deactivated and the segmented circuit 1100 enters sleep mode. In sleep mode, all of the circuit segments except the accelerometer 1122 and the safety processor 1104 are deactivated. The safety processor 1104 enters a low-power mode in which the safety processor 1104 only polls the accelerometer 1122. The safety processor 1104 monitors the accelerometer 1122 until the accelerometer 1122 detects movement, at which point the safety processor 1104 transitions the segmented circuit 1100 from sleep mode to the operational mode.

In some embodiments, the safety processor 1104 transitions the segmented circuit 1100 to the operational mode only when the accelerometer 1122 detects movement of the surgical instrument 2000 above a predetermined threshold. By responding only to movement above a predetermined threshold, the safety processor 1104 prevents inadvertent transition of the segmented circuit 1100 to operational mode when the surgical instrument 2000 is bumped or moved while stored. In some embodiments, the accelerometer 1122 is configured to monitor movement in a plurality of directions. For example, the accelerometer 1122 may be configured to detect movement in a first direction and a second direction. The safety processor 1104 monitors the accelerometer 1122 and transitions the segmented circuit 1100 from sleep mode to operational mode when movement above a predetermined threshold is detected in both the first direction and the second direction. By requiring movement above a predetermined threshold in at least two directions, the safety processor 1104 is configured to prevent inadvertent transition of the segmented circuit 1100 from sleep mode due to incidental movement during storage.

In some embodiments, the accelerometer 1122 is configured to detect movement in a first direction, a second direction, and a third direction. The safety processor 1104 monitors the accelerometer 1122 and is configured to transition the segmented circuit 1100 from sleep mode only when the accelerometer 1122 detects oscillating movement in each of the first direction, second direction, and third direction. In some embodiments, oscillating movement in each of a first direction, a second direction, and a third direction correspond to movement of the surgical instrument 2000 by an operator and therefore transition to the operational mode is desirable when the accelerometer 1122 detects oscillating movement in three directions.

In some embodiments, as the time since the last movement detected increases, the predetermined threshold of movement required to transition the segmented circuit 1100 from sleep mode also increases. For example, in some embodiments, the timer continues to operate during sleep mode. As the timer count increases, the safety processor 1104 increases the predetermined threshold of movement required to transition the segmented circuit 1100 to operational mode. The safety processor 1104 may increase the predetermined threshold to an upper limit. For example, in some embodiments, the safety processor 1104 transitions the segmented circuit 1100 to sleep mode and resets the timer. The predetermined threshold of movement is initially set to a low value, requiring only a minor movement of the surgical instrument 2000 to transition the segmented circuit 1100 from sleep mode. As the time since the transition to sleep mode, as measured by the timer, increases, the safety processor 1104 increases the predetermined threshold of movement. At a time T, the safety processor 1104 has increased the predetermined threshold to an upper limit. For all times T+, the predetermined threshold maintains a constant value of the upper limit.

In some embodiments, one or more additional and/or alternative sensors are used to transition the segmented circuit 1100 between sleep mode and operational mode. For example, in one embodiment, a touch sensor is located on the surgical instrument 2000. The touch sensor is coupled to the safety processor 1104 and/or the primary processor 1106. The touch sensor is configured to detect user contact with the surgical instrument 2000. For example, the touch sensor may be located on the handle of the surgical instrument 2000 to detect when an operator picks up the surgical instrument 2000. The safety processor 1104 transitions the segmented circuit 1100 to sleep mode after a predetermined period has passed without the accelerometer 1122 detecting movement. The safety processor 1104 monitors the touch sensor and transitions the segmented circuit 1100 to operational mode when the touch sensor detects user contact with the surgical instrument 2000. The touch sensor may comprise, for example, a capacitive touch sensor, a temperature sensor, and/or any other suitable touch sensor. In some embodiments, the touch sensor and the accelerometer 1122 may be used to transition the device between sleep mode and operation mode. For example, the safety processor 1104 may only transition the device to sleep mode when the accelerometer 1122 has not detected movement within a predetermined period and the touch sensor does not indicate a user is in contact with the surgical instrument 2000. Those skilled in the art will recognize that one or more additional sensors may be used to transition the segmented circuit 1100 between sleep mode and operational mode. In some embodiments, the touch sensor is only monitored by the safety processor 1104 when the segmented circuit 1100 is in sleep mode.

In some embodiments, the safety processor 1104 is configured to transition the segmented circuit 1100 from sleep mode to the operational mode when one or more handle controls are actuated. After transitioning to sleep mode, such as, for example, after the accelerometer 1122 has not detected movement for a predetermined period, the safety processor 1104 monitors one or more handle controls, such as, for example, the plurality of articulation switches 1158*a*-1164*b*. In other embodiments, the one or more handle controls comprise, for example, a clamp control 1166, a release button 1168, and/or any other suitable handle control. An operator of the surgical instrument 2000 may actuate one or more of the handle controls to transition the segmented circuit 1100 to operational mode. When the safety processor 1104 detects the actuation of a handle control, the safety processor 1104 initiates the transition of the segmented circuit 1100 to operational mode. Because the primary processor 1106 is in not active when the handle control is actuated, the operator can actuate the handle control without causing a corresponding action of the surgical instrument 2000.

Figure 16:
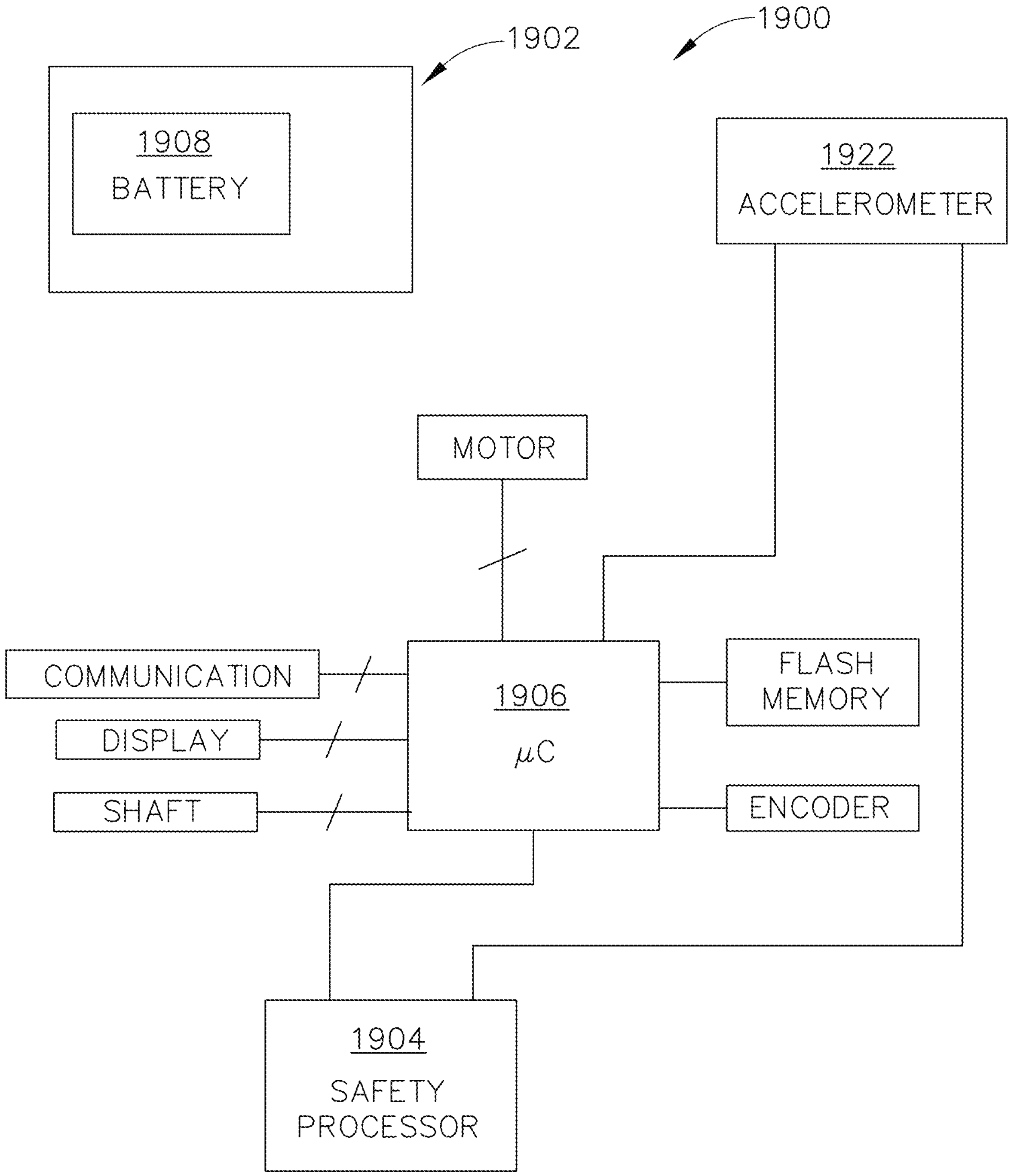
FIG. 16 illustrates one embodiment of a segmented circuit comprising an accelerometer.

FIG. 16 illustrates one embodiment of a segmented circuit 1900 comprising an accelerometer 1922 configured to monitor movement of a surgical instrument, such as, for example, the surgical instrument 2000 illustrated in FIGS. 1-3B. A power segment 1902 provides power from a battery 1908 to one or more circuit segments, such as, for example, the accelerometer 1922. The accelerometer 1922 is coupled to a processor 1906. The accelerometer 1922 is configured to monitor movement the surgical instrument 2000. The accelerometer 1922 is configured to generate one or more signals indicative of movement in one or more directions. For example, in some embodiments, the accelerometer 1922 is configured to monitor movement of the surgical instrument 2000 in three directions.

In certain instances, the processor 1906 may be an LM 4F230H5QR, available from Texas Instruments, for example. The processor 1906 is configured to monitor the accelerometer 1922 and transition the segmented circuit 1900 to sleep mode, for example, when no movement is detected within a predetermined time period. In some embodiments, the segmented circuit 1900 transitions to sleep mode after a predetermined period of inactivity. For example, a safety processor 1904 may transitions the segmented circuit 1900 to sleep mode after a predetermined period has passed without the accelerometer 1922 detecting movement. In certain instances, the accelerometer 1922 may be an LIS331DLM, available from STMicroelectronics, for example. A timer is in signal communication with the processor 1906. The timer may be integral with the processor 1906 and/or may be a separate circuit component. The timer is configured to count time since a last movement of the surgical instrument 2000 was detected by the accelerometer 1922. When the counter exceeds a predetermined threshold, the processor 1906 transitions the segmented circuit 1900 into sleep mode. In some embodiments, the timer is reset each time the accelerometer 1922 detects movement.

In some embodiments, the accelerometer 1922 is configured to detect an impact event. For example, when a surgical instrument 2000 is dropped, the accelerometer 1922 will detect acceleration due to gravity in a first direction and then a change in acceleration in a second direction (caused by impact with a floor and/or other surface). As another example, when the surgical instrument 2000 impacts a wall, the accelerometer 1922 will detect a spike in acceleration in one or more directions. When the accelerometer 1922 detects an impact event, the processor 1906 may prevent operation of the surgical instrument 2000, as impact events can loosen mechanical and/or electrical components. In some embodiments, only impacts above a predetermined threshold prevent operation. In other embodiments, all impacts are monitored and cumulative impacts above a predetermined threshold may prevent operation of the surgical instrument 2000.

With reference back to FIGS. 5A and 5B, in one embodiment, the segmented circuit 1100 comprises a power segment 1102*h*. The power segment 1102*h* is configured to provide a segment voltage to each of the circuit segments 1102*a*-1102*g*. The power segment 1102*h* comprises a battery 1108. The battery 1108 is configured to provide a predetermined voltage, such as, for example, 12 volts through battery connector 1110. One or more power converters 1114*a*, 1114*b*, 1116 are coupled to the battery 1108 to provide a specific voltage. For example, in the illustrated embodiments, the power segment 1102*h* comprises an axillary switching converter 1114*a*, a switching converter 1114*b*, and a low-drop out (LDO) converter 1116. The switch converters 1114*a*, 1114*b* are configured to provide 3.3 volts to one or more circuit components. The LDO converter 1116 is configured to provide 5.0 volts to one or more circuit components. In some embodiments, the power segment 1102*h* comprises a boost converter 1118. A transistor switch (e.g., N-Channel MOSFET) 1115 is coupled to the power converters 1114*b*, 1116. The boost converter 1118 is configured to provide an increased voltage above the voltage provided by the battery 1108, such as, for example, 13 volts. The boost converter 1118 may comprise, for example, a capacitor, an inductor, a battery, a rechargeable battery, and/or any other suitable boost converter for providing an increased voltage. The boost converter 1118 provides a boosted voltage to prevent brownouts and/or low-power conditions of one or more circuit segments 1102*a*-1102*g* during power-intensive operations of the surgical instrument 2000. The embodiments, however, are not limited to the voltage range(s) described in the context of this specification.

Figure 11:
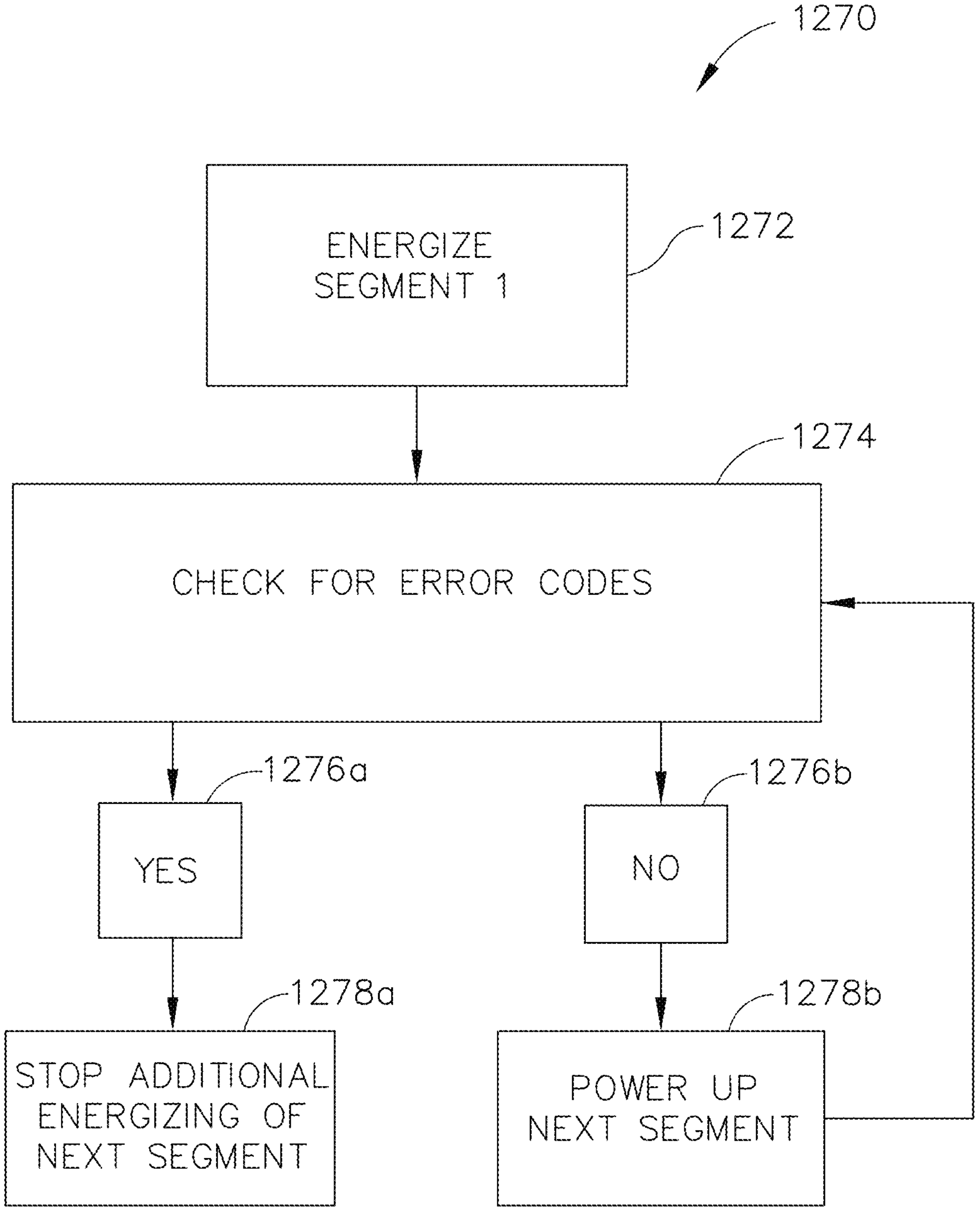
FIG. 11 illustrates one embodiment of a process for sequentially energizing a segmented circuit.

In some embodiments, the segmented circuit 1100 is configured for sequential start-up. An error check is performed by each circuit segment 1102*a*-1102*g* prior to energizing the next sequential circuit segment 1102*a*-1102*g*. FIG. 11 illustrates one embodiment of a process for sequentially energizing a segmented circuit 1270, such as, for example, the segmented circuit 1100. When a battery 1108 is coupled to the segmented circuit 1100, the safety processor 1104 is energized 1272. The safety processor 1104 performs a self-error check 1274. When an error is detected 1276*a*, the safety processor stops energizing the segmented circuit 1100 and generates an error code 1278*a*. When no errors are detected 1276*b*, the safety processor 1104 initiates 1278*b* power-up of the primary processor 1106. The primary processor 1106 performs a self-error check. When no errors are detected, the primary processor 1106 begins sequential power-up of each of the remaining circuit segments 1278*b*. Each circuit segment is energized and error checked by the primary processor 1106. When no errors are detected, the next circuit segment is energized 1278*b*. When an error is detected, the safety processor 1104 and/or the primary process stops energizing the current segment and generates an error 1278*a*. The sequential start-up continues until all of the circuit segments 1102*a*-1102*g* have been energized. In some embodiments, the segmented circuit 1100 transitions from sleep mode following a similar sequential power-up process 1250.

Figure 12:
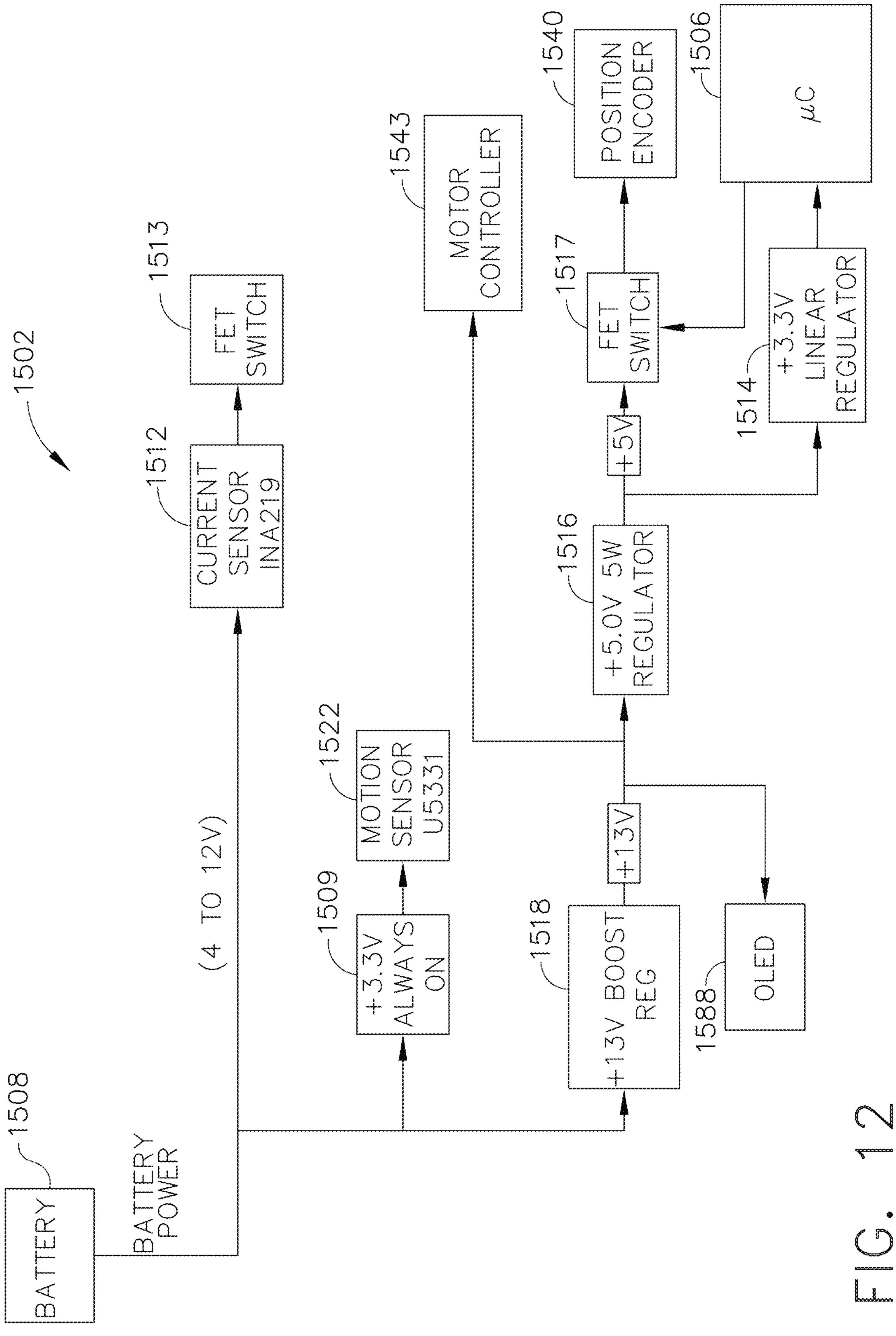
FIG. 12 illustrates one embodiment of a power segment comprising a plurality of daisy chained power converters.

FIG. 12 illustrates one embodiment of a power segment 1502 comprising a plurality of daisy chained power converters 1514, 1516, 1518. The power segment 1502 comprises a battery 1508. The battery 1508 is configured to provide a source voltage, such as, for example, 12V. A current sensor 1512 is coupled to the battery 1508 to monitor the current draw of a segmented circuit and/or one or more circuit segments. The current sensor 1512 is coupled to an FET switch 1513. The battery 1508 is coupled to one or more voltage converters 1509, 1514, 1516. An always on converter 1509 provides a constant voltage to one or more circuit components, such as, for example, a motion sensor 1522. The always on converter 1509 comprises, for example, a 3.3V converter. The always on converter 1509 may provide a constant voltage to additional circuit components, such as, for example, a safety processor (not shown). The battery 1508 is coupled to a boost converter 1518. The boost converter 1518 is configured to provide a boosted voltage above the voltage provided by the battery 1508. For example, in the illustrated embodiment, the battery 1508 provides a voltage of 12V. The boost converter 1518 is configured to boost the voltage to 13V. The boost converter 1518 is configured to maintain a minimum voltage during operation of a surgical instrument, for example, the surgical instrument 2000 illustrated in FIGS. 1-3B. Operation of a motor can result in the power provided to the primary processor 1506 dropping below a minimum threshold and creating a brownout or reset condition in the primary processor 1506. The boost converter 1518 ensures that sufficient power is available to the primary processor 1506 and/or other circuit components, such as the motor controller 1543, during operation of the surgical instrument 2000. In some embodiments, the boost converter 1518 is coupled directly one or more circuit components, such as, for example, an OLED display 1588.

The boost converter 1518 is coupled to a one or more step-down converters to provide voltages below the boosted voltage level. A first voltage converter 1516 is coupled to the boost converter 1518 and provides a first stepped-down voltage to one or more circuit components. In the illustrated embodiment, the first voltage converter 1516 provides a voltage of 5V. The first voltage converter 1516 is coupled to a rotary position encoder 1540. A FET switch 1517 is coupled between the first voltage converter 1516 and the rotary position encoder 1540. The FET switch 1517 is controlled by the processor 1506. The processor 1506 opens the FET switch 1517 to deactivate the position encoder 1540, for example, during power intensive operations. The first voltage converter 1516 is coupled to a second voltage converter 1514 configured to provide a second stepped-down voltage. The second stepped-down voltage comprises, for example, 3.3V. The second voltage converter 1514 is coupled to a processor 1506. In some embodiments, the boost converter 1518, the first voltage converter 1516, and the second voltage converter 1514 are coupled in a daisy chain configuration. The daisy chain configuration allows the use of smaller, more efficient converters for generating voltage levels below the boosted voltage level. The embodiments, however, are not limited to the particular voltage range(s) described in the context of this specification.

Figure 13:
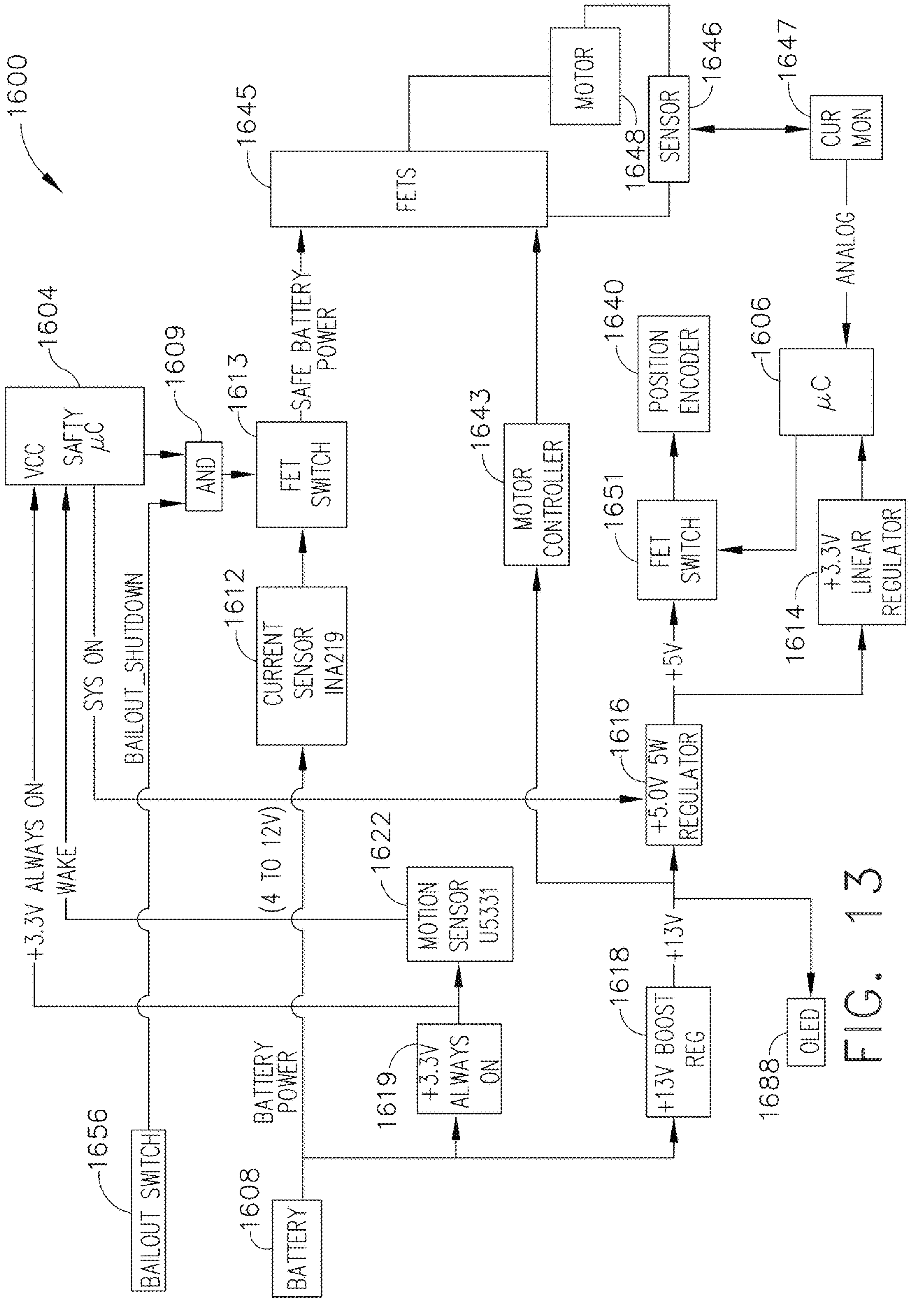
FIG. 13 illustrates one embodiment of a segmented circuit configured to maximize power available for critical and/or power intense functions.

FIG. 13 illustrates one embodiment of a segmented circuit 1600 configured to maximize power available for critical and/or power intense functions. The segmented circuit 1600 comprises a battery 1608. The battery 1608 is configured to provide a source voltage such as, for example, 12V. The source voltage is provided to a plurality of voltage converters 1619, 1618. An always-on voltage converter 1619 provides a constant voltage to one or more circuit components, for example, a motion sensor 1622 and a safety processor 1604. The always-on voltage converter 1619 is directly coupled to the battery 1608. The always-on converter 1619 provides a voltage of, for example, 3.3V. The embodiments, however, are not limited to the particular voltage range(s) described in the context of this specification.

The segmented circuit 1600 comprises a boost converter 1618. The boost converter 1618 provides a boosted voltage above the source voltage provided by the battery 1608, such as, for example, 13V. The boost converter 1618 provides a boosted voltage directly to one or more circuit components, such as, for example, an OLED display 1688 and a motor controller 1643. By coupling the OLED display 1688 directly to the boost converter 1618, the segmented circuit 1600 eliminates the need for a power converter dedicated to the OLED display 1688. The boost converter 1618 provides a boosted voltage to the motor controller 1643 and the motor 1648 during one or more power intensive operations of the motor 1648, such as, for example, a cutting operation. The boost converter 1618 is coupled to a step-down converter 1616. The step-down converter 1616 is configured to provide a voltage below the boosted voltage to one or more circuit components, such as, for example, 5V. The step-down converter 1616 is coupled to, for example, an FET switch 1651 and a position encoder 1640. The FET switch 1651 is coupled to the primary processor 1606. The primary processor 1606 opens the FET switch 1651 when transitioning the segmented circuit 1600 to sleep mode and/or during power intensive functions requiring additional voltage delivered to the motor 1648. Opening the FET switch 1651 deactivates the position encoder 1640 and eliminates the power draw of the position encoder 1640. The embodiments, however, are not limited to the particular voltage range(s) described in the context of this specification.

The step-down converter 1616 is coupled to a linear converter 1614. The linear converter 1614 is configured to provide a voltage of, for example, 3.3V. The linear converter 1614 is coupled to the primary processor 1606. The linear converter 1614 provides an operating voltage to the primary processor 1606. The linear converter 1614 may be coupled to one or more additional circuit components. The embodiments, however, are not limited to the particular voltage range(s) described in the context of this specification.

The segmented circuit 1600 comprises a bailout switch 1656. The bailout switch 1656 is coupled to a bailout door on the surgical instrument 2000. The bailout switch 1656 and the safety processor 1604 are coupled to an AND gate 1609. The AND gate 1609 provides an input to a FET switch 1613. When the bailout switch 1656 detects a bailout condition, the bailout switch 1656 provides a bailout shutdown signal to the AND gate 1609. When the safety processor 1604 detects an unsafe condition, such as, for example, due to a sensor mismatch, the safety processor 1604 provides a shutdown signal to the AND gate 1609. In some embodiments, both the bailout shutdown signal and the shutdown signal are high during normal operation and are low when a bailout condition or an unsafe condition is detected. When the output of the AND gate 1609 is low, the FET switch 1613 is opened and operation of the motor 1648 is prevented. In some embodiments, the safety processor 1604 utilizes the shutdown signal to transition the motor 1648 to an off state in sleep mode. A third input to the FET switch 1613 is provided by a current sensor 1612 coupled to the battery 1608. The current sensor 1612 monitors the current drawn by the circuit 1600 and opens the FET switch 1613 to shut-off power to the motor 1648 when an electrical current above a predetermined threshold is detected. The FET switch 1613 and the motor controller 1643 are coupled to a bank of FET switches 1645 configured to control operation of the motor 1648.

A motor current sensor 1646 is coupled in series with the motor 1648 to provide a motor current sensor reading to a current monitor 1647. The current monitor 1647 is coupled to the primary processor 1606. The current monitor 1647 provides a signal indicative of the current draw of the motor 1648. The primary processor 1606 may utilize the signal from the motor current 1647 to control operation of the motor, for example, to ensure the current draw of the motor 1648 is within an acceptable range, to compare the current draw of the motor 1648 to one or more other parameters of the circuit 1600 such as, for example, the position encoder 1640, and/or to determine one or more parameters of a treatment site. In some embodiments, the current monitor 1647 may be coupled to the safety processor 1604.

In some embodiments, actuation of one or more handle controls, such as, for example, a firing trigger, causes the primary processor 1606 to decrease power to one or more components while the handle control is actuated. For example, in one embodiment, a firing trigger controls a firing stroke of a cutting member. The cutting member is driven by the motor 1648. Actuation of the firing trigger results in forward operation of the motor 1648 and advancement of the cutting member. During firing, the primary processor 1606 closes the FET switch 1651 to remove power from the position encoder 1640. The deactivation of one or more circuit components allows higher power to be delivered to the motor 1648. When the firing trigger is released, full power is restored to the deactivated components, for example, by closing the FET switch 1651 and reactivating the position encoder 1640.

In some embodiments, the safety processor 1604 controls operation of the segmented circuit 1600. For example, the safety processor 1604 may initiate a sequential power-up of the segmented circuit 1600, transition of the segmented circuit 1600 to and from sleep mode, and/or may override one or more control signals from the primary processor 1606. For example, in the illustrated embodiment, the safety processor 1604 is coupled to the step-down converter 1616. The safety processor 1604 controls operation of the segmented circuit 1600 by activating or deactivating the step-down converter 1616 to provide power to the remainder of the segmented circuit 1600.

Figure 14:
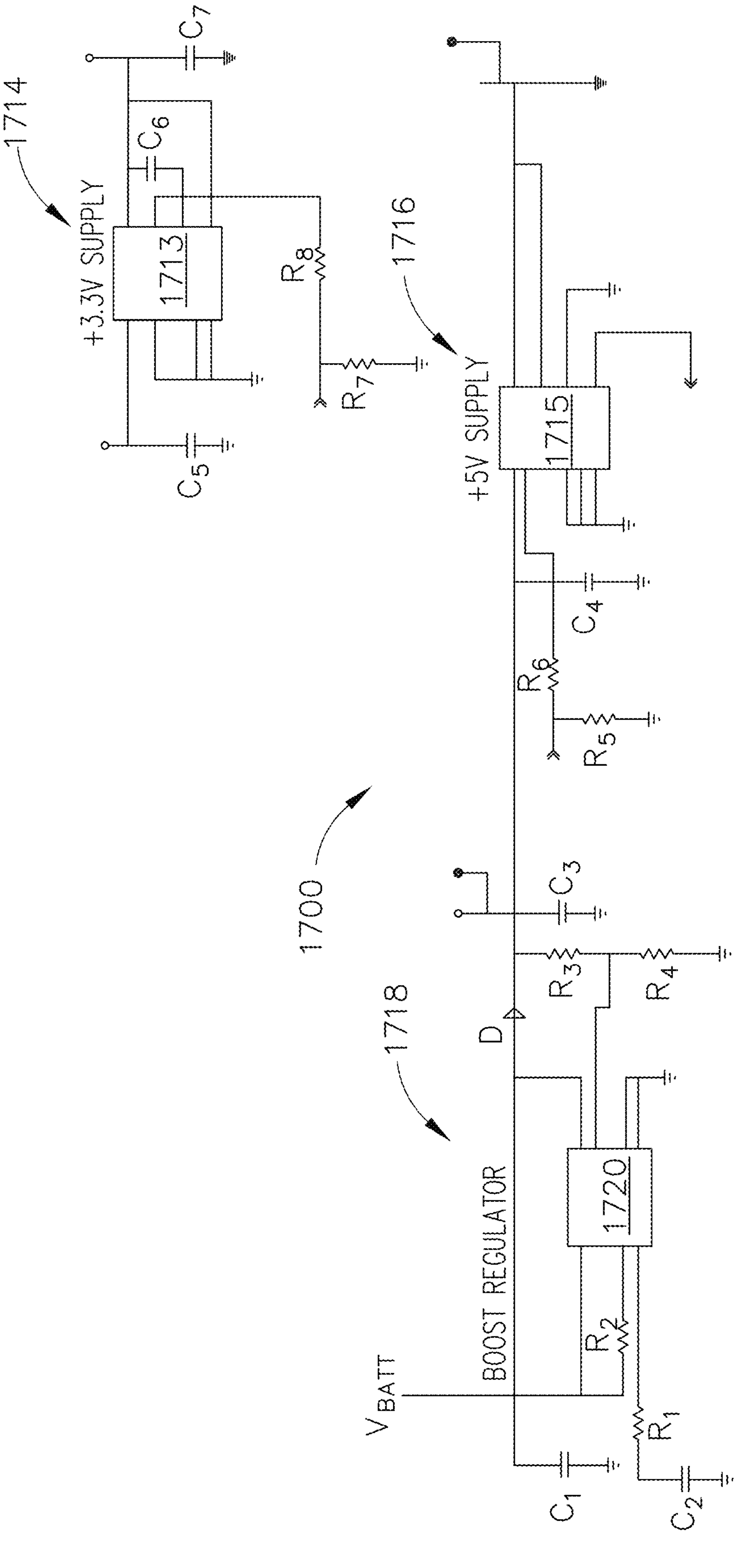
FIG. 14 illustrates one embodiment of a power system comprising a plurality of daisy chained power converters configured to be sequentially energized.

FIG. 14 illustrates one embodiment of a power system 1700 comprising a plurality of daisy chained power converters 1714, 1716, 1718 configured to be sequentially energized. The plurality of daisy chained power converters 1714, 1716, 1718 may be sequentially activated by, for example, a safety processor during initial power-up and/or transition from sleep mode. The safety processor may be powered by an independent power converter (not shown). For example, in one embodiment, when a battery voltage $V_{BATT}$ is coupled to the power system 1700 and/or an accelerometer detects movement in sleep mode, the safety processor initiates a sequential start-up of the daisy chained power converters 1714, 1716, 1718. The safety processor activates the 13V boost section 1718. The boost section 1718 is energized and performs a self-check. In some embodiments, the boost section 1718 comprises an integrated circuit 1720 configured to boost the source voltage and to perform a self check. A diode D prevents power-up of a 5V supply section 1716 until the boost section 1718 has completed a self-check and provided a signal to the diode D indicating that the boost section 1718 did not identify any errors. In some embodiments, this signal is provided by the safety processor. The embodiments, however, are not limited to the particular voltage range(s) described in the context of this specification.

The 5V supply section 1716 is sequentially powered-up after the boost section 1718. The 5V supply section 1716 performs a self-check during power-up to identify any errors in the 5V supply section 1716. The 5V supply section 1716 comprises an integrated circuit 1715 configured to provide a step-down voltage from the boost voltage and to perform an error check. When no errors are detected, the 5V supply section 1716 completes sequential power-up and provides an activation signal to the 3.3V supply section 1714. In some embodiments, the safety processor provides an activation signal to the 3.3V supply section 1714. The 3.3V supply section comprises an integrated circuit 1713 configured to provide a step-down voltage from the 5V supply section 1716 and perform a self-error check during power-up. When no errors are detected during the self-check, the 3.3V supply section 1714 provides power to the primary processor. The primary processor is configured to sequentially energize each of the remaining circuit segments. By sequentially energizing the power system 1700 and/or the remainder of a segmented circuit, the power system 1700 reduces error risks, allows for stabilization of voltage levels before loads are applied, and prevents large current draws from all hardware being turned on simultaneously in an uncontrolled manner. The embodiments, however, are not limited to the particular voltage range(s) described in the context of this specification.

In one embodiment, the power system 1700 comprises an over voltage identification and mitigation circuit. The over voltage identification and mitigation circuit is configured to detect a monopolar return current in the surgical instrument and interrupt power from the power segment when the monopolar return current is detected. The over voltage identification and mitigation circuit is configured to identify ground floatation of the power system. The over voltage identification and mitigation circuit comprises a metal oxide varistor. The over voltage identification and mitigation circuit comprises at least one transient voltage suppression diode.

Figure 15:
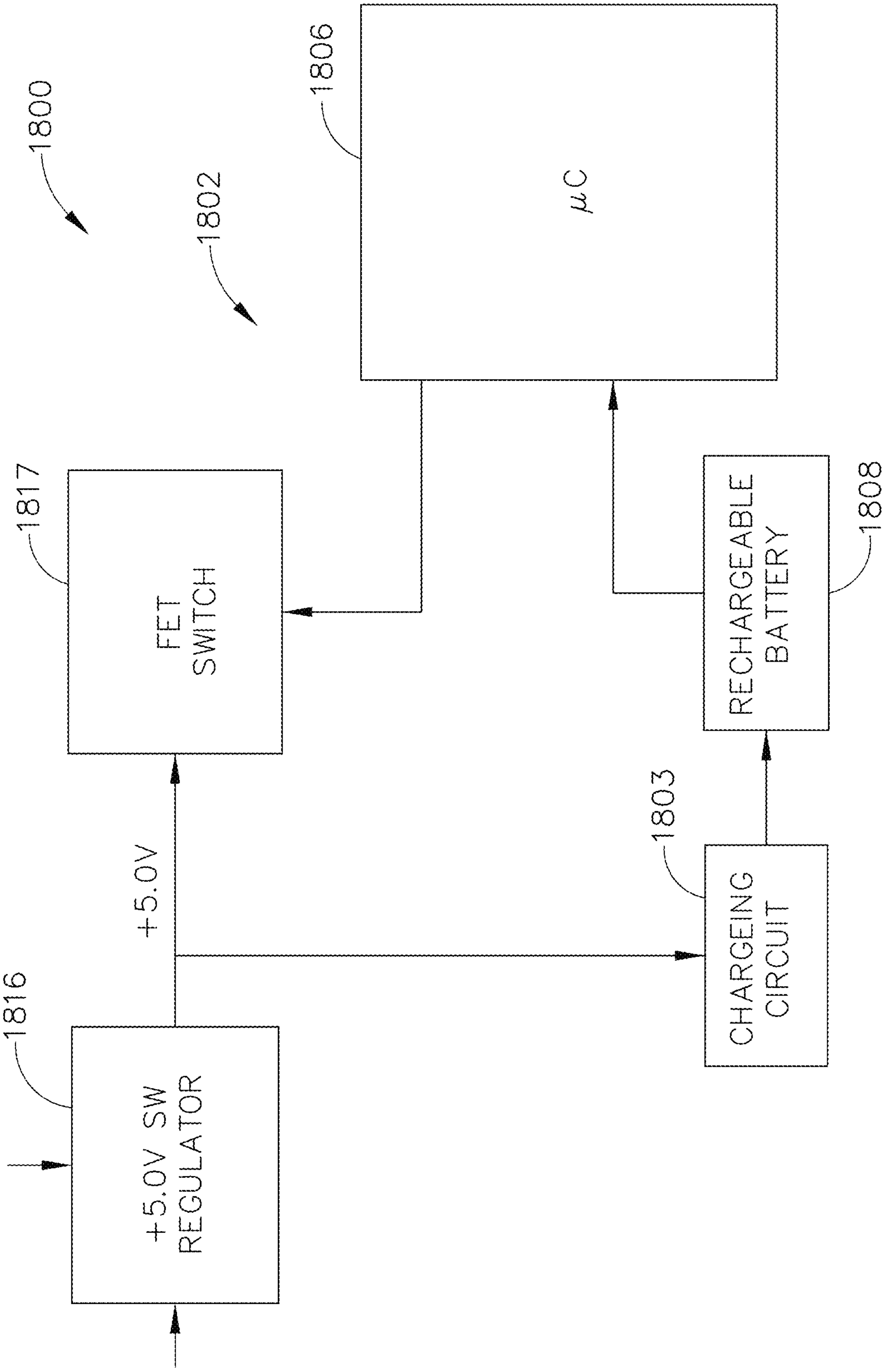
FIG. 15 illustrates one embodiment of a segmented circuit comprising an isolated control section.

FIG. 15 illustrates one embodiment of a segmented circuit 1800 comprising an isolated control section 1802. The isolated control section 1802 isolates control hardware of the segmented circuit 1800 from a power section (not shown) of the segmented circuit 1800. The control section 1802 comprises, for example, a primary processor 1806, a safety processor (not shown), and/or additional control hardware, for example, a FET Switch 1817. The power section comprises, for example, a motor, a motor driver, and/or a plurality of motor MOSFETS. The isolated control section 1802 comprises a charging circuit 1803 and a rechargeable battery 1808 coupled to a 5V power converter 1816. The charging circuit 1803 and the rechargeable battery 1808 isolate the primary processor 1806 from the power section. In some embodiments, the rechargeable battery 1808 is coupled to a safety processor and any additional support hardware. Isolating the control section 1802 from the power section allows the control section 1802, for example, the primary processor 1806, to remain active even when main power is removed, provides a filter, through the rechargeable battery 1808, to keep noise out of the control section 1802, isolates the control section 1802 from heavy swings in the battery voltage to ensure proper operation even during heavy motor loads, and/or allows for real-time operating system (RTOS) to be used by the segmented circuit 1800. In some embodiments, the rechargeable battery 1808 provides a stepped-down voltage to the primary processor, such as, for example, 3.3V. The embodiments, however, are not limited to the particular voltage range(s) described in the context of this specification.

Figure 17:
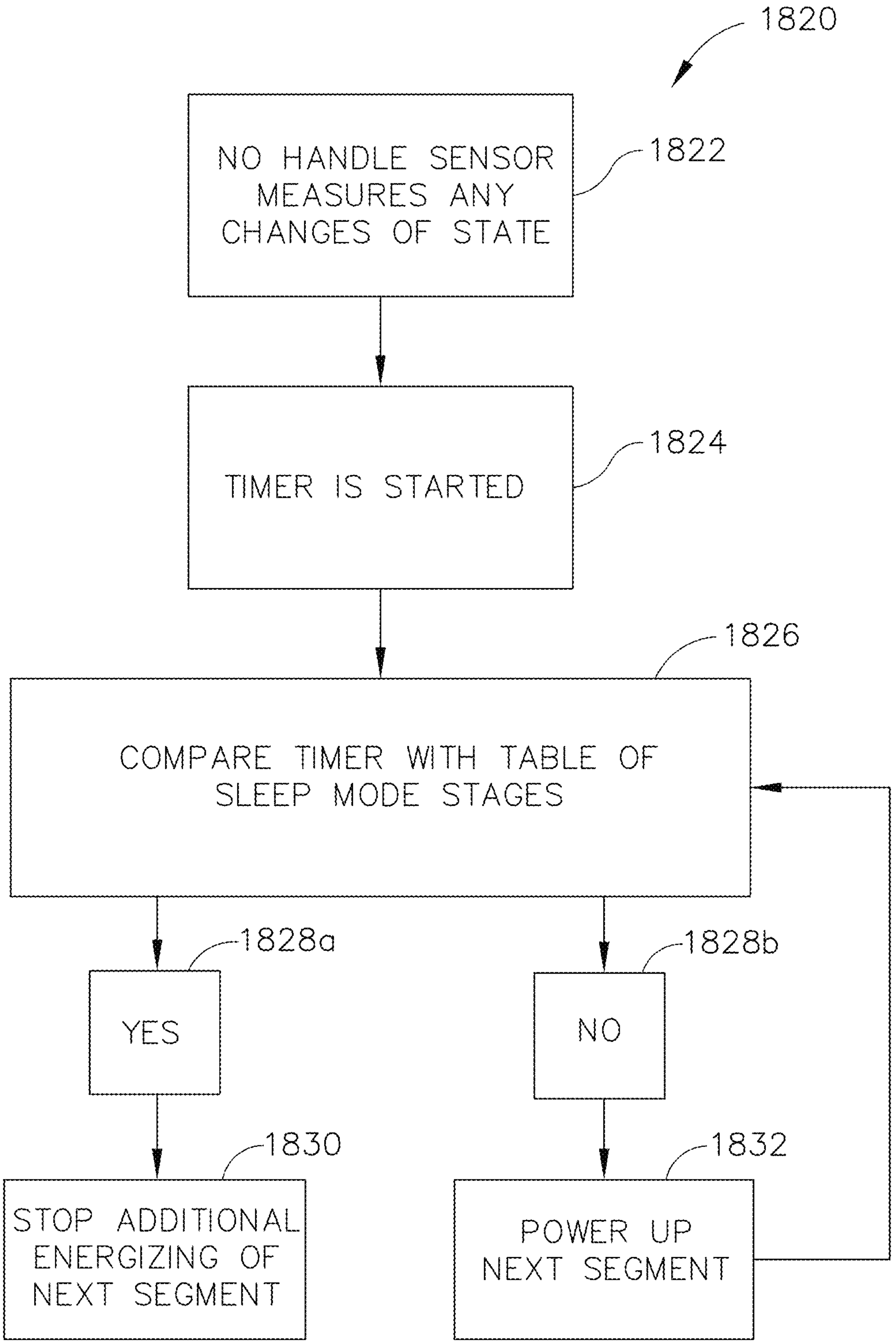
FIG. 17 illustrates one embodiment of a process for sequential start-up of a segmented circuit.

FIG. 17 illustrates one embodiment of a process for sequential start-up of a segmented circuit, such as, for example, the segmented circuit 1100 illustrated in FIGS. 5A and 5B. The sequential start-up process 1820 begins when one or more sensors initiate a transition from sleep mode to operational mode. When the one or more sensors stop detecting state changes 1822, a timer is started 1824. The timer counts the time since the last movement/interaction with the surgical instrument 2000 was detected by the one or more sensors. The timer count is compared 1826 to a table of sleep mode stages by, for example, the safety processor 1104. When the timer count exceeds one or more counts for transition to a sleep mode stage 1828*a*, the safety processor 1104 stops energizing 1830 the segmented circuit 1100 and transitions the segmented circuit 1100 to the corresponding sleep mode stage. When the timer count is below the threshold for any of the sleep mode stages 1828*b*, the segmented circuit 1100 continues to sequentially energize the next circuit segment 1832.

With reference back to FIGS. 5A and 5B, in some embodiments, the segmented circuit 1100 comprises one or more environmental sensors to detect improper storage and/or treatment of a surgical instrument. For example, in one embodiment, the segmented circuit 1100 comprises a temperature sensor. The temperature sensor is configured to detect the maximum and/or minimum temperature that the segmented circuit 1100 is exposed to. The surgical instrument 2000 and the segmented circuit 1100 comprise a design limit exposure for maximum and/or minimum temperatures. When the surgical instrument 2000 is exposed to temperatures exceeding the limits, for example, a temperature exceeding the maximum limit during a sterilization technique, the temperature sensor detects the overexposure and prevents operation of the device. The temperature sensor may comprise, for example, a bi-metal strip configured to disable the surgical instrument 2000 when exposed to a temperature above a predetermined threshold, a solid-state temperature sensor configured to store temperature data and provide the temperature data to the safety processor 1104, and/or any other suitable temperature sensor.

In some embodiments, the accelerometer 1122 is configured as an environmental safety sensor. The accelerometer 1122 records the acceleration experienced by the surgical instrument 2000. Acceleration above a predetermined threshold may indicate, for example, that the surgical instrument has been dropped. The surgical instrument comprises a maximum acceleration tolerance. When the accelerometer 1122 detects acceleration above the maximum acceleration tolerance, safety processor 1104 prevents operation of the surgical instrument 2000.

In some embodiments, the segmented circuit 1100 comprises a moisture sensor. The moisture sensor is configured to indicate when the segmented circuit 1100 has been exposed to moisture. The moisture sensor may comprise, for example, an immersion sensor configured to indicate when the surgical instrument 2000 has been fully immersed in a cleaning fluid, a moisture sensor configured to indicate when moisture is in contact with the segmented circuit 1100 when the segmented circuit 1100 is energized, and/or any other suitable moisture sensor.

In some embodiments, the segmented circuit 1100 comprises a chemical exposure sensor. The chemical exposure sensor is configured to indicate when the surgical instrument 2000 has come into contact with harmful and/or dangerous chemicals. For example, during a sterilization procedure, an inappropriate chemical may be used that leads to degradation of the surgical instrument 2000. The chemical exposure sensor may indicate inappropriate chemical exposure to the safety processor 1104, which may prevent operation of the surgical instrument 2000.

The segmented circuit 1100 is configured to monitor a number of usage cycles. For example, in one embodiment, the battery 1108 comprises a circuit configured to monitor a usage cycle count. In some embodiments, the safety processor 1104 is configured to monitor the usage cycle count. Usage cycles may comprise surgical events initiated by a surgical instrument, such as, for example, the number of shafts 2004 used with the surgical instrument 2000, the number of cartridges inserted into and/or deployed by the surgical instrument 2000, and/or the number of firings of the surgical instrument 2000. In some embodiments, a usage cycle may comprise an environmental event, such as, for example, an impact event, exposure to improper storage conditions and/or improper chemicals, a sterilization process, a cleaning process, and/or a reconditioning process. In some embodiments, a usage cycle may comprise a power assembly (e.g., battery pack) exchange and/or a charging cycle.

The segmented circuit 1100 may maintain a total usage cycle count for all defined usage cycles and/or may maintain individual usage cycle counts for one or more defined usage cycles. For example, in one embodiment, the segmented circuit 1100 may maintain a single usage cycle count for all surgical events initiated by the surgical instrument 2000 and individual usage cycle counts for each environmental event experienced by the surgical instrument 2000. The usage cycle count is used to enforce one or more behaviors by the segmented circuit 1100. For example, usage cycle count may be used to disable a segmented circuit 1100, for example, by disabling a battery 1108, when the number of usage cycles exceeds a predetermined threshold or exposure to an inappropriate environmental event is detected. In some embodiments, the usage cycle count is used to indicate when suggested and/or mandatory service of the surgical instrument 2000 is necessary.

Figure 18:
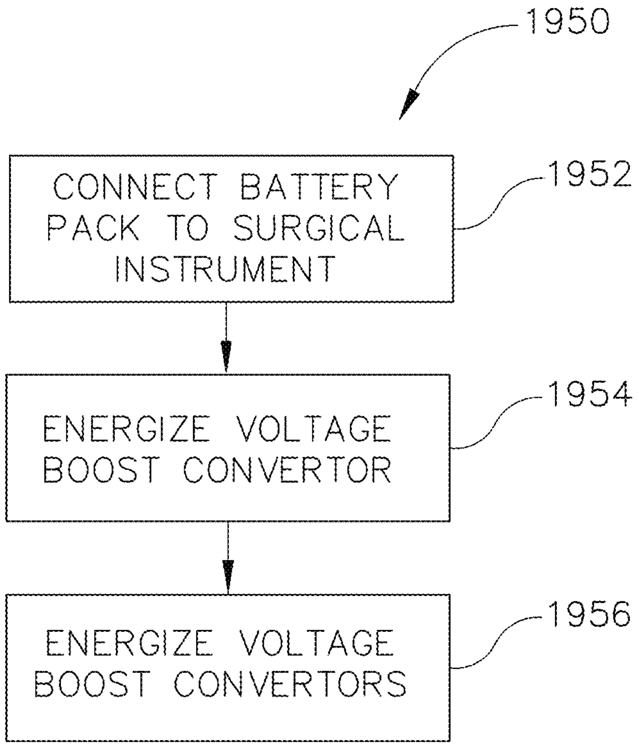
FIG. 18 illustrates one embodiment of a method 1950 for controlling a surgical instrument comprising a segmented circuit, such as, for example, the segmented control circuit 1602 illustrated in FIG. 12.

FIG. 18 illustrates one embodiment of a method 1950 for controlling a surgical instrument comprising a segmented circuit, such as, for example, the segmented control circuit 1602 illustrated in FIG. 12. At 1952, a power assembly 1608 is coupled to the surgical instrument. The power assembly 1608 may comprise any suitable battery, such as, for example, the power assembly 2006 illustrates in FIGS. 1-3B. The power assembly 1608 is configured to provide a source voltage to the segmented control circuit 1602. The source voltage may comprise any suitable voltage, such as, for example, 12V. At 1954, the power assembly 1608 energizes a voltage boost convertor 1618. The voltage boost convertor 1618 is configured to provide a set voltage. The set voltage comprises a voltage greater than the source voltage provided by the power assembly 1608. For example, in some embodiments, the set voltage comprises a voltage of 13V. In a third step 1956, the voltage boost convertor 1618 energizes one or more voltage regulators to provide one or more operating voltages to one or more circuit components. The operating voltages comprise a voltage less than the set voltage provided by the voltage boost convertor.

In some embodiments, the boost convertor 1618 is coupled to a first voltage regulator 1616 configured to provide a first operating voltage. The first operating voltage provided by the first voltage regulator 1616 is less than the set voltage provided by the voltage boost convertor. For example, in some embodiments, the first operating voltage comprises a voltage of 5V. In some embodiments, the boost convertor is coupled to a second voltage regulator 1614. The second voltage regulator 1614 is configured to provide a second operating voltage. The second operating voltage comprises a voltage less than the set voltage and the first operating voltage. For example, in some embodiments, the second operating voltage comprises a voltage of 3.3V. In some embodiments, the battery 1608, voltage boost convertor 1618, first voltage regulator 1616, and second voltage regulator 1614 are configured in a daisy chain configuration. The battery 1608 provides the source voltage to the voltage boost convertor 1618. The voltage boost convertor 1618 boosts the source voltage to the set voltage. The voltage boost convertor 1618 provides the set voltage to the first voltage regulator 1616. The first voltage regulator 1616 generates the first operating voltage and provides the first operating voltage to the second voltage regulator 1614. The second voltage regulator 1614 generates the second operating voltage.

In some embodiments, one or more circuit components are energized directly by the voltage boost convertor 1618. For example, in some embodiments, an OLED display 1688 is coupled directly to the voltage boost convertor 1618. The voltage boost convertor 1618 provides the set voltage to the OLED display 1688, eliminating the need for the OLED to have a power generator integral therewith. In some embodiments, a processor, such as, for example, the safety processor 1604 illustrated in FIGS. 5A and 5B, verifies the voltage provided by the voltage boost convertor 1618 and/or the one or more voltage regulators 1616, 1614. The safety processor 1604 is configured to verify a voltage provided by each of the voltage boost convertor 1618 and the voltage regulators 1616, 1614. In some embodiments, the safety processor 1604 verifies the set voltage. When the set voltage is equal to or greater than a first predetermined value, the safety processor 1604 energizes the first voltage regulator 1616. The safety processor 1604 verifies the first operational voltage provided by the first voltage regulator 1616. When the first operational voltage is equal to or greater than a second predetermined value, the safety processor 1604 energizes the second voltage regulator 1614. The safety processor 1604 then verifies the second operational voltage. When the second operational voltage is equal to or greater than a third predetermined value, the safety processor 1604 energizes each of the remaining circuit components of the segmented circuit 1600.

Various aspects of the subject matter described herein relate to methods of controlling power management of a surgical instrument through a segmented circuit and variable voltage protection. In one embodiment, a method of controlling power management in a surgical instrument comprising a primary processor, a safety processor, and a segmented circuit comprising a plurality of circuit segments in signal communication with the primary processor, the plurality of circuit segments comprising a power segment, the method comprising providing, by the power segment, variable voltage control of each segment. In one embodiment, the method comprises providing, by the power segment comprising a boost converter, power stabilization for at least one of the segment voltages. The method also comprises providing, by the boost converter, power stabilization to the primary processor and the safety processor. The method also comprises providing, by the boost converter, a constant voltage to the primary processor and the safety processor above a predetermined threshold independent of a power draw of the plurality of circuit segments. The method also comprises detecting, by an over voltage identification and mitigation circuit, a monopolar return current in the surgical instrument and interrupting power from the power segment when the monopolar return current is detected. The method also comprises identifying, by the over voltage identification and mitigation circuit, ground floatation of the power system.

In another embodiment, the method also comprises energizing, by the power segment, each of the plurality of circuit segments sequentially and error checking each circuit segment prior to energizing a sequential circuit segment. The method also comprises energizing the safety processor by a power source coupled to the power segment, performing an error check, by the safety processor, when the safety processor is energized, and performing, and energizing, the safety processor, the primary processor when no errors are detected during the error check. The method also comprises performing an error check, by the primary processor when the primary processor is energized, and wherein when no errors are detected during the error check, sequentially energizing, by the primary processor, each of the plurality of circuit segments. The method also comprises error checking, by the primary processor, each of the plurality of circuit segments.

In another embodiment, the method comprises, energizing, by the boost convertor the safety processor when a power source is connected to the power segment, performing, by the safety processor an error check, and energizing the primary processor, by the safety processor, when no errors are detected during the error check. The method also comprises performing an error check, by the primary process, and sequentially energizing, by the primary processor, each of the plurality of circuit segments when no errors are detected during the error check. The method also comprises error checking, by the primary processor, each of the plurality of circuit segments.

In another embodiment, the method also comprises, providing, by a power segment, a segment voltage to the primary processor, providing variable voltage protection of each segment, providing, by a boost converter, power stabilization for at least one of the segment voltages, an over voltage identification, and a mitigation circuit, energizing, by the power segment, each of the plurality of circuit segments sequentially, and error checking each circuit segment prior to energizing a sequential circuit segment.

Various aspects of the subject matter described herein relate to methods of controlling an surgical instrument control circuit having a safety processor. In one embodiment, a method of controlling a surgical instrument comprising a control circuit comprising a primary processor, a safety processor in signal communication with the primary processor, and a segmented circuit comprising a plurality of circuit segments in signal communication with the primary processor, the method comprising monitoring, by the safety processor, one or more parameters of the plurality of circuit segments. The method also comprises verifying, by the safety processor, the one or more parameters of the plurality of circuit segments and verifying the one or more parameters independently of one or more control signals generated by the primary processor. The method further comprises verifying, by the safety processor, a velocity of a cutting element. The method also comprises monitoring, by a first sensor, a first property of the surgical instrument, monitoring, by a second sensor a second property of the surgical instrument, wherein the first property and the second property comprise a predetermined relationship, and wherein the first sensor and the second sensor are in signal communication with the safety processor. The method also comprises preventing, by the safety processor, operation of at least one of the plurality of circuit segments when the fault is detected, wherein a fault comprises the first property and the second property having values inconsistent with the predetermined relationship. The method also comprises, monitoring, by a Hall-effect sensor, a cutting member position and monitoring, by a motor current sensor, a motor current.

In another embodiment, the method comprises disabling, by the safety processor, at least one of the plurality of circuit segments when a mismatch is detected between the verification of the one or more parameters and the one or more control signals generated by the primary processor. The method also comprises preventing by the safety processor, operation of a motor segment and interrupting power flow to the motor segment from the power segment. The method also comprises preventing, by the safety processor, forward operation of a motor segment and when the fault is detected allowing, by the safety processor, reverse operation of the motor segment.

In another embodiment the segmented circuit comprises a motor segment and a power segment, the method comprising controlling, by the motor segment, one or more mechanical operations of the surgical instrument and monitoring, by the safety processor, one or more parameters of the plurality of circuit segments. The method also comprises verifying, by the safety processor, the one or more parameters of the plurality of circuit segments and the independently verifying, by the safety processor, the one or more parameters independently of one or more control signals generated by the primary processor.

In another embodiment, the method also comprises independently verifying, by the safety processor, the velocity of a cutting element. The method also comprises monitoring, by a first sensor, a first property of the surgical instrument, monitoring, by a second sensor, a second property of the surgical instrument, wherein the first property and the second property comprise a predetermined relationship, and wherein the first sensor and the second sensor are in signal communication with the safety processor, wherein a fault comprises the first property and the second property having values inconsistent with the predetermined relationship, and preventing, by the safety processor, the operation of at least one of the plurality of circuit segments when the fault is detected by the safety processor. The method also comprises monitoring, by a Hall-effect sensor, a cutting member position and monitoring, by a motor current sensor, a motor current.

In another embodiment, the method comprises disabling, by the safety processor, at least one of the plurality of circuit segments when a mismatch is detected between the verification of the one or more parameters and the one or more control signals generated by the primary processor. The method also comprises preventing, by the safety processor, operation of the motor segment and interrupting power flow to the motor segment from the power segment. The method also comprises preventing, by the safety processor, forward operation of the motor segment and allowing, by the safety processor, reverse operation of the motor segment when the fault is detected.

In another embodiment, the method comprises monitoring, by the safety processor, one or more parameters of the plurality of circuit segments, verifying, by the safety processor, the one or more parameters of the plurality of circuit segments, verifying, by the safety processor, the one or more parameters independently of one or more control signals generated by the primary processor, and disabling, by the safety processor, at least one of the plurality of circuit segments when a mismatch is detected between the verification of the one or more parameters and the one or more control signals generated by the primary processor. The method also comprises monitoring, by a first sensor, a first property of the surgical instrument, monitoring, by a second sensor, a second property of the surgical instrument, wherein the first property and the second property comprise a predetermined relationship, and wherein the first sensor and the second sensor are in signal communication with the safety processor, wherein a fault comprises the first property and the second property having values inconsistent with the predetermined relationship, and wherein when the fault is detected, preventing, by the safety processor, operation of at least one of the plurality of circuit segments. The method also comprises preventing, by the safety processor, operation of a motor segment by interrupting power flow to the motor segment from the power segment when a fault is detected prevent.

Various aspects of the subject matter described herein relate to methods of controlling power management of a surgical instrument through sleep options of segmented circuit and wake up control, the surgical instrument comprising a control circuit comprising a primary processor, a safety processor in signal communication with the primary processor, and a segmented circuit comprising a plurality of circuit segments in signal communication with the primary processor, the plurality of circuit segments comprising a power segment, the method comprising transitioning, by the safety processor, the primary processor and at least one of the plurality of circuit segments from an active mode to a sleep mode and from the sleep mode to the active mode. The method also comprises tracking, by a timer, a time from a last user initiated event and wherein when the time from the last user initiated event exceeds a predetermined threshold, transitioning, by the safety processor, the primary processor and at least one of the plurality of circuit segments to the sleep mode. The method also comprises detecting, by an acceleration segment comprising an accelerometer, one or more movements of the surgical instrument. The method also comprises tracking, by the timer, a time from the last movement detected by the acceleration segment. The method also comprises maintaining, by the safety processor, the acceleration segment in the active mode when transitioning the plurality of circuit segments to the sleep mode.

In another embodiment, the method also comprises transitioning to the sleep mode in a plurality of stages. The method also comprises transitioning the segmented circuit to a first stage after a first predetermined period and dimming a backlight of the display segment, transitioning the segmented circuit to a second stage after a second predetermined period and turning the backlight off, transitioning the segmented circuit to a third stage after a third predetermined period and reducing a polling rate of the accelerometer, and transitioning the segmented circuit to a fourth stage after a fourth predetermined period and turning a display off and transitioning the surgical instrument to the sleep mode.

In another embodiment comprising detecting, by a touch sensor, user contact with a surgical instrument and transitioning, by the safety processor, the primary processor and a plurality of circuit segments from a sleep mode to an active mode when the touch sensor detects a user in contact with surgical instrument. The method also comprises monitoring, by the safety processor, at least one handle control and transitioning, by the safety processor, the primary processor and the plurality of circuit segments from the sleep mode to the active mode when the at least one handle control is actuated.

In another embodiment, the method comprises transitioning, by the safety processor, the surgical device to the active mode when the accelerometer detects movement of the surgical instrument above a predetermined threshold. The method also comprises monitoring, by the safety processor, the accelerometer for movement in at least a first direction and a second direction and transitioning, by the safety processor, the surgical instrument from the sleep mode to the operational mode when movement above a predetermined threshold is detected in at least the first direction and the second direction. The method also comprises monitoring, by the safety processor, the accelerometer for oscillating movement above the predetermined threshold in the first direction, the second direction, and a third direction, and transitioning, by the safety processor, the surgical instrument from the sleep mode to the operational mode when oscillating movement is detected above the predetermined threshold in the first direction, second direction, and third direction. The method also comprises increasing the predetermined as the time from the previous movement increases.

In another embodiment, the method comprises transitioning, by the safety processor, the primary processor and at least one of the plurality of circuit segments from an active mode to a sleep mode and from the sleep mode to the active mode when a time from the last user initiated event exceeds a predetermined threshold, tracking, by a timer, a time from the last movement detected by the acceleration segment, and transitioning, by the safety processor, the surgical device to the active mode when the acceleration segment detects movement of the surgical instrument above a predetermined threshold.

In another embodiment, a method of controlling a surgical instrument comprises tracking a time from a last user initiated event and disabling, by the safety processor, a backlight of a display when the time from the last user initiated event exceeds a predetermined threshold. The method also comprises flashing, by the safety processor, the backlight of the display to indicate to a user to look at the display.

Various aspects of the subject matter described herein relate to methods of verifying the sterilization of a surgical instrument through a sterilization verification circuit, the surgical instrument comprising a control circuit comprising a primary processor, a safety processor in signal communication with the primary processor and a segmented circuit comprising a plurality of circuit segments in signal communication with the primary processor, the plurality of circuit segments comprising a storage verification segment, the method comprising indicating when a surgical instrument has been properly stored and sterilized. The method also comprises detecting, by at least one sensor, one or more improper storage or sterilization parameters. The method also comprises sensing, by a drop protection sensor, when the instrument has been dropped and preventing, by the safety processor, operation of at least one of the plurality of circuit segments when the drop protection sensor detects that the surgical instrument has been dropped. The method also comprises preventing, by the safety processor, operation of at least one of the plurality of circuit segments when a temperature above a predetermined threshold is detected by a temperature sensor. The method also comprises preventing, by the safety processor, operation of at least one of the plurality of circuit segments when the temperature sensor detects a temperature above a predetermined threshold.

In another embodiment, the method comprises controlling, by the safety processor, operation of at least one of the plurality of circuit segments when a moisture detection sensor detects moisture. The method also comprises detecting, by a moisture detection sensor, an autoclave cycle and preventing, by the safety processor, operation of the surgical instrument unless the autoclave cycle has been detected. The method also comprises preventing, by the safety processor, operation of the at least one of the plurality of circuit segments when moisture is detected during a staged circuit start-up.

In another embodiment, the method comprises indicating, by the plurality of circuit segments comprising a sterilization verification segment, when a surgical instrument has been properly sterilized. The method also comprises detecting, by at least one sensor of the sterilization verification segment, sterilization of the surgical instrument. The method also comprises indicating, by a storage verification segment, when a surgical instrument has been properly stored. The method also comprises detecting, by at least one sensor of the storage verification segment, improper storage of the surgical instrument.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2010, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

In accordance with various embodiments, the surgical instruments described herein may comprise one or more processors (e.g., microprocessor, microcontroller) coupled to various sensors. In addition, to the processor(s), a storage (having operating logic) and communication interface, are coupled to each other.

As described earlier, the sensors may be configured to detect and collect data associated with the surgical device. The processor processes the sensor data received from the sensor(s).

The processor may be configured to execute the operating logic. The processor may be any one of a number of single or multi-core processors known in the art. The storage may comprise volatile and non-volatile storage media configured to store persistent and temporal (working) copy of the operating logic.

In various embodiments, the operating logic may be configured to process the collected biometric associated with motion data of the user, as described above. In various embodiments, the operating logic may be configured to perform the initial processing, and transmit the data to the computer hosting the application to determine and generate instructions. For these embodiments, the operating logic may be further configured to receive information from and provide feedback to a hosting computer. In alternate embodiments, the operating logic may be configured to assume a larger role in receiving information and determining the feedback. In either case, whether determined on its own or responsive to instructions from a hosting computer, the operating logic may be further configured to control and provide feedback to the user.

In various embodiments, the operating logic may be implemented in instructions supported by the instruction set architecture (ISA) of the processor, or in higher level languages and compiled into the supported ISA. The operating logic may comprise one or more logic units or modules. The operating logic may be implemented in an object oriented manner. The operating logic may be configured to be executed in a multi-tasking and/or multi-thread manner. In other embodiments, the operating logic may be implemented in hardware such as a gate array.

In various embodiments, the communication interface may be configured to facilitate communication between a peripheral device and the computing system. The communication may include transmission of the collected biometric data associated with position, posture, and/or movement data of the user's body part(s) to a hosting computer, and transmission of data associated with the tactile feedback from the host computer to the peripheral device. In various embodiments, the communication interface may be a wired or a wireless communication interface. An example of a wired communication interface may include, but is not limited to, a Universal Serial Bus (USB) interface. An example of a wireless communication interface may include, but is not limited to, a Bluetooth interface.

For various embodiments, the processor may be packaged together with the operating logic. In various embodiments, the processor may be packaged together with the operating logic to form a System in Package (SiP). In various embodiments, the processor may be integrated on the same die with the operating logic. In various embodiments, the processor may be packaged together with the operating logic to form a System on Chip (SoC).

Various embodiments may be described herein in the general context of computer executable instructions, such as software, program modules, and/or engines being executed by a processor. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, program modules, and/or engines may be located in both local and remote computer storage media including memory storage devices. A memory such as a random access memory (RAM) or other dynamic storage device may be employed for storing information and instructions to be executed by the processor. The memory also may be used for storing temporary variables or other intermediate information during execution of instructions to be executed by the processor.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more of the modules described herein may comprise one or more embedded applications implemented as firmware, software, hardware, or any combination thereof. One or more of the modules described herein may comprise various executable modules such as software, programs, data, drivers, application program interfaces (APIs), and so forth. The firmware may be stored in a memory of the controller 2016 and/or the controller 2022 which may comprise a nonvolatile memory (NVM), such as in bit-masked read-only memory (ROM) or flash memory. In various implementations, storing the firmware in ROM may preserve flash memory. The nonvolatile memory (NVM) may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

It is worthy to note that any reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The disclosed embodiments have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that when a specific number of an introduced claim recitation is intended, such an intent will be explicitly recited in the claim, and in the absence of such recitation no such intent is present. For example, as an aid to understanding, the following appended claims may contain usage of the introductory phrases “at least one” and “one or more” to introduce claim recitations. However, the use of such phrases should not be construed to imply that the introduction of a claim recitation by the indefinite articles “a” or “an” limits any particular claim containing such introduced claim recitation to claims containing only one such recitation, even when the same claim includes the introductory phrases “one or more” or “at least one” and indefinite articles such as “a” or “an” (e.g., “a” and/or “an” should typically be interpreted to mean “at least one” or “one or more”); the same holds true for the use of definite articles used to introduce claim recitations.

In addition, even when a specific number of an introduced claim recitation is explicitly recited, those skilled in the art will recognize that such recitation should typically be interpreted to mean at least the recited number (e.g., the bare recitation of “two recitations,” without other modifiers, typically means at least two recitations, or two or more recitations). Furthermore, in those instances where a convention analogous to “at least one of A, B, and C, etc.” is used, in general such a construction is intended in the sense one having skill in the art would understand the convention (e.g., “a system having at least one of A, B, and C” would include but not be limited to systems that have A alone, B alone, C alone, A and B together, A and C together, B and C together, and/or A, B, and C together, etc.). In those instances where a convention analogous to “at least one of A, B, or C, etc.” is used, in general such a construction is intended in the sense one having skill in the art would understand the convention (e.g., “a system having at least one of A, B, or C” would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase “A or B” will be typically understood to include the possibilities of “A” or “B” or “A and B.”

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like “responsive to,” “related to,” or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A surgical instrument, comprising:

a motor;

a power source coupled to the motor;

a knife movable by an operation of the motor;

a motor current sensor configured to produce a first signal for monitoring a current draw of the motor from the power source;

a knife position sensor configured to produce a second signal for monitoring a position of the knife;

a primary processor; and a safety processor coupled to the motor, the motor current sensor, the knife position sensor, and the primary processor, wherein the safety processor is configured to:

indicate to the primary processor that the first signal and the second signal are consistent with a predetermined relationship for the current draw of the motor and the position of the knife; and indicate an unsafe condition to the primary processor based on detecting that the first signal and the second signal are inconsistent with the predetermined relationship for the current draw of the motor and the position of the knife, wherein the primary processor is configured to prevent the operation of the motor based on the indication of the unsafe condition from the safety processor.

2. The surgical instrument of claim 1, wherein the primary processor is configured to prevent the operation of the motor by interrupting a motor segment coupled to the motor.

3. The surgical instrument of claim 2, further comprising a switch, wherein the switch is configured to control an operation of the motor segment, and wherein, independent of the primary processor, the safety processor is configured to prevent the operation of the motor by opening the switch to prevent the operation of the motor segment based on the safety processor detecting that the first signal and the second signal are inconsistent with the predetermined relationship.

4. The surgical instrument of claim 1, wherein the safety processor and the primary processor are configured to implement a redundant safety check by exchanging periodic status signals at a predetermined interval.

5. The surgical instrument of claim 4, wherein the periodic status signals indicate that the first signal and the second signal are consistent with the predetermined relationship.

6. A surgical instrument, comprising:

a motor;

a power source coupled to the motor;

a firing bar movable by an operation of the motor;

a first sensor configured to measure a first parameter associated with the operation of the motor;

a second sensor configured to measure a second parameter associated with an operation of the firing bar;

a first processor; and a second processor coupled to the motor, the first sensor, the second sensor, and the first processor, wherein the second processor is configured to:

indicate to the first processor that the first parameter associated with the operation of the motor and the second parameter associated with the operation of the firing bar satisfy a predetermined relationship; and indicate an unsafe condition to the first processor based on the second processor detecting that the first parameter associated with the operation of the motor and the second parameter associated with the operation of the firing bar do not satisfy the predetermined relationship, wherein the first processor is configured to prevent the operation of the motor based on the indication of the unsafe condition from the second processor.

7. The surgical instrument of claim 6, wherein the first processor is configured to prevent the operation of the motor by interrupting a motor segment coupled to the motor.

8. The surgical instrument of claim 7, further comprising a switch, wherein the switch is configured to control an operation of the motor segment, and wherein, independent of the first processor, the second processor is configured to prevent the operation of the motor by opening the switch to prevent the operation of the motor segment based on the second processor detecting the first parameter and the second parameter do not satisfy the predetermined relationship.

9. The surgical instrument of claim 6, wherein the second processor and the first processor are configured to implement a redundant safety check by exchanging periodic signals at a predetermined interval.

10. The surgical instrument of claim 9, wherein the periodic signals indicate that the first parameter and the second parameter satisfy the predetermined relationship.

11. The surgical instrument of claim 6, wherein the first parameter measured by the first sensor comprises a current draw of the motor from the power source.

12. The surgical instrument of claim 6, wherein the second parameter measured by the second sensor comprises one of a real-time velocity of the firing bar or a real-time position of the firing bar.

13. A surgical instrument, comprising:

a motor;

a knife movable by an actuation of the motor;

a first sensor configured to monitor a motor speed;

a second sensor configured to monitor a knife position;

a primary processor; and a safety processor coupled to the motor, the first sensor, the second sensor, and the primary processor, wherein the safety processor is configured to:

determine a knife speed based on the knife position; and indicate an unsafe condition to the primary processor based on determining the knife speed and the motor speed are inconsistent with a predetermined relationship, wherein the primary processor is configured to prevent the actuation of the motor based on the indication of the unsafe condition from the safety processor.

14. The surgical instrument of claim 13, wherein the safety processor is configured to indicate normal condition to the primary processor based on determining the knife speed and the motor speed are consistent with the predetermined relationship.

15. The surgical instrument of claim 13, wherein the primary processor is configured to prevent the actuation of the motor by decoupling the motor from a power source.

16. The surgical instrument of claim 13, wherein, independent of the primary processor, the safety processor is configured to prevent the actuation of the motor based on determining the knife speed and the motor speed are inconsistent with the predetermined relationship.

17. The surgical instrument of claim 13, wherein the primary processor and the safety processor are configured to implement a redundant safety check by exchanging periodic signals at a predetermined interval.

18. The surgical instrument of claim 17, wherein the periodic signals indicate that the knife speed and the motor speed are consistent with the predetermined relationship.

19. The surgical instrument of claim 13, wherein the primary processor is configured to indicate an intended motor direction to the safety processor, and wherein the safety processor is configured to indicate the unsafe condition to the primary processor based on determining that any one or more of the knife speed, the motor speed, and the intended motor direction are inconsistent with the predetermined relationship.

20. The surgical instrument of claim 13, wherein the safety processor is configured to reset the primary processor based on determining the knife speed and the motor speed are inconsistent with the predetermined relationship.

* * * * *